United States Patent
Kuramoto et al.

(10) Patent No.: US 9,854,996 B2
(45) Date of Patent: Jan. 2, 2018

(54) MEDICAL IMAGE PROCESSING DEVICE, METHOD FOR OPERATING THE SAME, AND ENDOSCOPE SYSTEM

(71) Applicant: FUJIFILM Corporation, Tokyo (JP)

(72) Inventors: Masayuki Kuramoto, Ashigarakami-gun (JP); Makoto Sugizaki, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 270 days.

(21) Appl. No.: 14/752,651

(22) Filed: Jun. 26, 2015

(65) Prior Publication Data

US 2015/0374263 A1 Dec. 31, 2015

(30) Foreign Application Priority Data

Jun. 27, 2014 (JP) ................. 2014-133391

(51) Int. Cl.
| | |
|---|---|
| *A61B 5/103* | (2006.01) |
| *A61B 5/00* | (2006.01) |
| *A61B 1/00* | (2006.01) |
| *A61B 1/06* | (2006.01) |
| *G06T 7/00* | (2017.01) |
| *G06T 7/90* | (2017.01) |

(52) U.S. Cl.
CPC .......... *A61B 5/1032* (2013.01); *A61B 1/0005* (2013.01); *A61B 1/00009* (2013.01); *A61B 1/0684* (2013.01); *A61B 5/0075* (2013.01); *A61B 5/0084* (2013.01); *G06T 7/0012* (2013.01); *G06T 7/90* (2017.01); *G06T 2207/10068* (2013.01); *G06T 2207/30092* (2013.01); *G06T 2207/30096* (2013.01)

(58) Field of Classification Search
CPC .................................................... A61B 5/1032
See application file for complete search history.

(56) References Cited

U.S. PATENT DOCUMENTS

| | | | | |
|---|---|---|---|---|
| 4,860,091 A | * | 8/1989 | Kimura | ................... H04N 9/77 348/30 |
| 2004/0225223 A1 | * | 11/2004 | Honda | ............... A61B 1/00045 600/476 |

FOREIGN PATENT DOCUMENTS

JP 3228627 B2 11/2001

\* cited by examiner

*Primary Examiner* — Michael Kahelin

(74) *Attorney, Agent, or Firm* — Birch, Stewart, Kolasch & Birch, LLP

(57) ABSTRACT

First RGB image signals are inputted. Color difference signals Cr and Cb are calculated from the first RGB image signals. In a feature space formed by the color difference signals Cr and Cb, a first process and a second process are performed. In the first process, coordinates which correspond to the first, second, and third observation areas are moved in a parallel manner such that the coordinates which correspond to the second observation area are moved to a reference area that contains the origin point. In the second process, the coordinates which correspond to the first observation area and the coordinates which correspond to the third observation area are moved away from each other.

18 Claims, 36 Drawing Sheets ab SPACE FORMED BY COLOR COMPONENTS a*, b* OF CIE Lab SPACE ab SPACE FORMED BY COLOR COMPONENTS a*, b* OF CIE Lab SPACE ab SPACE FORMED BY COLOR COMPONENTS a*, b* OF CIE Lab SPACE ab SPACE FORMED BY COLOR COMPONENTS a*, b* OF CIE Lab SPACE

MEDICAL IMAGE PROCESSING DEVICE, METHOD FOR OPERATING THE SAME, AND ENDOSCOPE SYSTEM

CROSS-REFERENCE TO RELATED APPLICATIONS

The present application claims priority under 35 U.S.C. §119 to Japanese Patent Application No. 2014-133391, filed Jun. 27, 2014. Each of the above application(s) is hereby expressly incorporated by reference, in its entirety, into the present application.

BACKGROUND OF THE INVENTION

1. Field of the Invention

The present invention relates to a medical image processing device for producing an image in which a difference in color between a normal site and a lesion site is enhanced, a method for operating a medical image processing device, and an endoscope system.

2. Description Related to the Prior Art

In medical fields, diagnoses utilizing endoscope systems have been widely performed. The endoscope system comprises a light source device, an endoscope, and a processor device. In the endoscope system, illumination light is applied from the endoscope to a region of interest (object) and the object under the illumination light is imaged with an imaging element of the endoscope. An image of the object is displayed on a monitor based on image signals obtained by imaging the object. A doctor detects the presence or absence of a lesion while observing the image displayed on the monitor.

It is easy to detect a lesion (e.g. protrusion from mucosal surface) which significantly differs from a normal site (normal portion) in shape and size. However, with regard to a lesion which is similar to the normal portion in shape and size, the lesion is detected based on a difference in color from that of the normal portion. It is extremely difficult to detect the lesion in a case where the lesion is in its early stage and there is little difference in color between the lesion and the normal portion. In Japanese Patent No. 3228627, a difference in color between the normal portion and the lesion is made clearly visible by a process to further move a portion which is displaced from a reference value of blood volume (hemoglobin index) away from the reference value. It is known that gastric (stomach) cancer causes atrophy of gastric mucosa (mucous membrane layer of the stomach), which makes the color of the gastric mucosa to fade. For this reason, there is a difference in color between the atrophic mucosa and the normal mucosa. The stomach cancer is diagnosed by observing the difference in color between the suspected lesion and the normal portion with an endoscope. "ABC method (ABC screening)" is recommended by the authorized nonprofit organization "Japan Research Foundation of Prediction, Diagnosis and Therapy for Gastric Cancer".

In advanced stages of atrophy (for example, groups C or D in the ABC screening), the difference in color between the normal portion and the atrophic portion is clear, so that it is easy to detect the atrophic portion. However, in intermediate stages (for example, groups B and C in the ABC screening), there is little difference in color between the atrophic portion and the normal portion. Therefore it is difficult to detect the atrophic portion based only on the difference in color. It is necessary to enhance the difference in color between the atrophic portion and the normal portion to facilitate the detection of the atrophic portion even if there is little difference in color between them.

Note that the difference in color between the atrophic portion and the normal portion may be enhanced using a method described in Japanese Patent No. 3228627. However, the color of the atrophic portion is affected not only by the blood volume but also by factors other than the blood volume. Therefore it is difficult to enhance the difference in color between the atrophic portion and the normal portion with the use of the method described in the Japanese Patent No. 3228627.

SUMMARY OF THE INVENTION

An object of the present invention is to provide a medical image processing device for producing an image in which a difference in color between an abnormal portion such as an atrophic portion with atrophic gastric mucosa and a normal portion is enhanced, a method for operating a medical image processing device, and an endoscope system.

A medical image processing device according to the present invention comprises an input processing unit, a color information obtaining section, and a first movement processor. The input processing unit performs an input process of a first color image signal. The color information obtaining section obtains two or more pieces of color information from the first color image signal. The first movement processor moves coordinates within a feature space from first, second, and third observation areas so as to move the coordinates from a specific observation area to a reference area defined in the feature space and moves the coordinates within the feature space from the two observation areas, other than the specific observation area, out of the first to third observation areas, to be away from each other. The feature space is formed by the two or more pieces of color information. The specific observation area is one of the first to third observation areas. Objects of interest are distributed in the first, second, and third observation areas.

It is preferred that the feature space is a Cb-Cr space formed by color difference signals Cr and Cb, being the two or more pieces of color information, or an ab space formed by color components a* and b*, being the two or more pieces of color information, of CIE Lab space. It is preferred that, within the feature space, the first movement processor moves the coordinates in a parallel manner from the first, second, and third observation areas so as to move the coordinates from the specific observation area to the reference area and changes angles of the coordinates located in the two observation areas, other than the specific observation area, out of the first to third observation areas so as to move the coordinates from the two observation areas to be away from each other. It is preferred that the reference area includes an origin point of the feature space but excludes the two observation areas other than the specific observation area.

It is preferred that the two or more pieces of color information are hue H and saturation S, and the feature space is an HS space formed by the hue H and the saturation S. It is preferred that, within the HS space, the first movement processor moves the coordinates in a parallel manner in a saturation direction from the first, second, and third observation areas so as to move the coordinates from the specific observation area to the reference area and moves the coordinates in a hue direction from the two observation areas, other than the specific observation area, out of the first to third observation areas, to be away from each other. It is preferred that the reference area includes an origin point of the HS space but excludes the two observation areas other than the specific observation area.

It is preferred that the medical image processing device further comprises a second movement processor for moving the coordinates within the feature space from the second observation area to the reference area while the coordinates in the first and third observation areas are maintained unchanged and for moving the coordinates within the feature space from the third observation area while the coordinates in the first observation area are maintained unchanged.

It is preferred that the feature space is Cb-Cr space formed by color difference signals Cr and Cb, being the two or more pieces of color information, or an ab space formed by color components a* and b*, being the two or more pieces of color information, of CIE Lab space. It is preferred that, in the feature space, the second movement processor changes a radial coordinate of the coordinates in the second observation area to move the coordinates from the second observation area to the reference area while the coordinates in the first and third observation areas are maintained unchanged, and changes an angle of the coordinates in the third observation area to move the coordinates from the third observation area while the coordinates in the first observation area are maintained unchanged and while the coordinates moved from the second observation area are maintained in the reference area.

It is preferred that the two or more pieces of color information are hue H and saturation S, and the feature space is an HS space formed by the hue H and the saturation S. It is preferred that, within the HS space, the second movement processor moves the coordinates in a saturation direction from the second observation area to the reference area while the coordinates in the first and third observation areas are maintained unchanged and moves the coordinates in a hue direction from the third observation area while the coordinates in the first observation area are maintained unchanged and while the coordinates moved from the second observation area are maintained in the reference area. It is preferred that the reference area includes an origin point of the HS space but excludes the first observation area and the third observation area.

It is preferred that the medical image processing device further comprises a color image signal converter and a brightness adjuster. The color image signal converter converts the two or more pieces of color information, which have been processed through the first movement processor or the second movement processor, into a second color image signal. The brightness adjuster adjusts a pixel value of the second color image signal based on first brightness information obtained from the first color image signal and second brightness information obtained from the second color image signal.

It is preferred that the first color image signal is three color image signals. It is preferred that, in the feature space, a difference between the first observation area and the second observation area of a case where at least one of the three color image signals is a narrowband signal is greater than a difference between the first observation area and the second observation area of a case where all of the three color image signals are broadband signals, or a difference between the first observation area and the third observation area of the case where at least one of the three color image signals is a narrowband signal is greater than a difference between the first observation area and the third observation area of the case where all of the three color image signals are broadband signals.

An endoscope system comprises the above-described medical image processing device according to the present invention and a display unit. The display unit displays a first special image obtained from two or more pieces of color information processed by the first movement processor and a second special image obtained from two or more pieces of color information processed by the second movement processor.

A method for operating a medical image processing device comprises an input processing step, a color information obtaining step, and a movement processing step. In the input processing step, an input processing unit performs an input process of a first color image signal. In the color information obtaining step, a color information obtaining section obtains two or more pieces of color information from the first color image signal. In the movement processing step, a first movement processor moves coordinates within a feature space from first, second, and third observation areas so as to move the coordinates from a specific observation area to a reference area defined in the feature space and moves the coordinates within the feature space from the two observation areas, other than the specific observation area, out of the first to third observation areas, to be away from each other. The feature space is formed by the two or more pieces of color information. The specific observation area is one of the first to third observation areas. Objects of interest are distributed in the first, second, and third observation areas.

According to the present invention, an image in which a difference in color between an abnormal portion (e.g. an atrophic portion with an atrophic gastric mucosa) and a normal portion is enhanced is produced.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

First Embodiment

Figure 1:
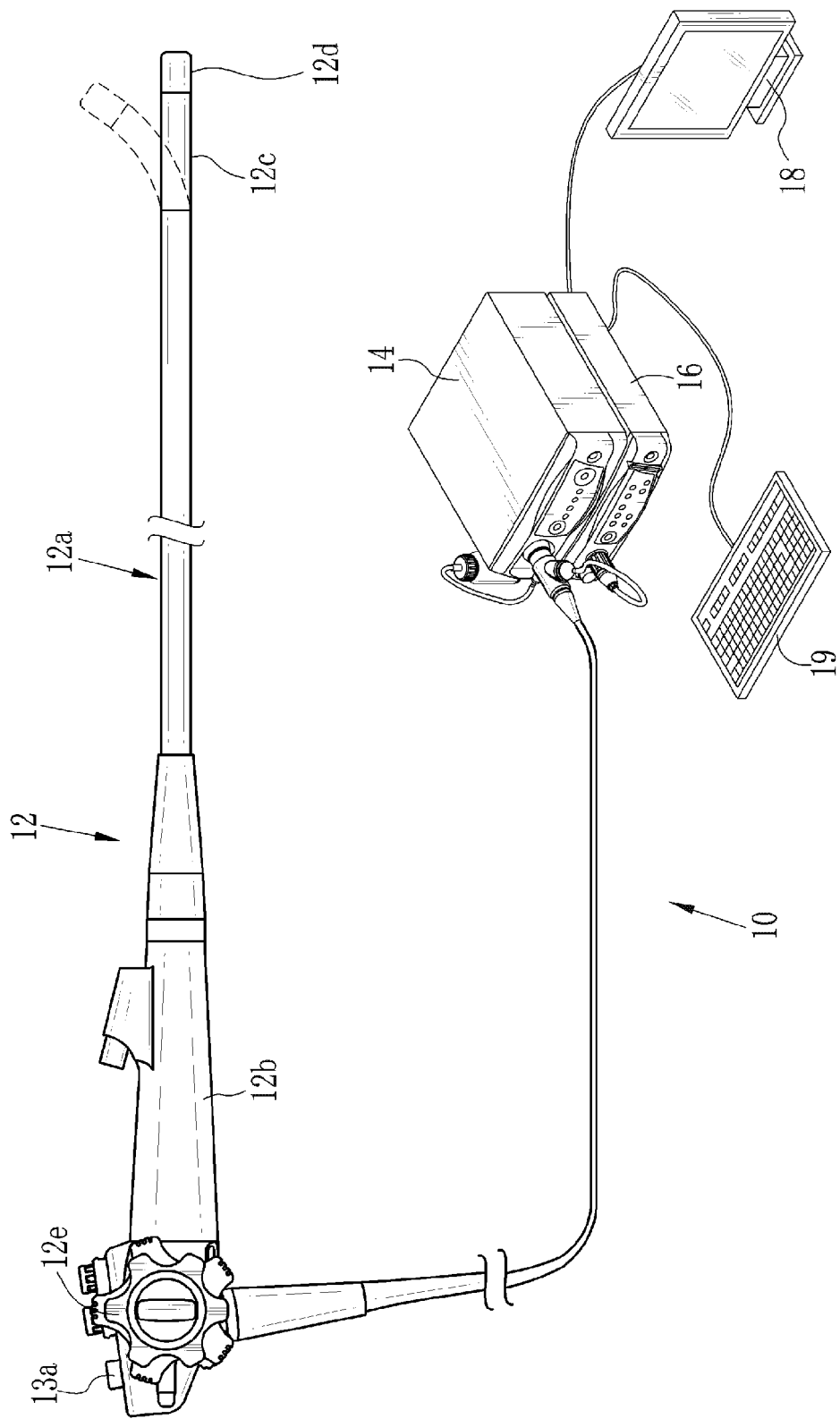
FIG. 1 is an external view of an endoscope system according to a first embodiment.

As illustrated in FIG. 1, an endoscope system 10 of a first embodiment comprises an endoscope 12, a light source device 14, a processor device 16, a monitor (display unit) 18, and a console 19. The endoscope 12 is connected optically to the light source device 14, and electrically to the processor device 16. The endoscope 12 comprises an insertion section 12a to be inserted into a body cavity, a control handle unit 12b provided at the proximal end of the insertion section 12a, a flexible portion 12c, and a distal portion 12d. The distal portion 12d is coupled to the flexible portion 12c, which is provided on the distal side of the insertion section 12a. The flexible portion 12c is bent by operating an angle knob 12e of the control handle unit 12b. The distal portion 12d is directed to a desired direction by bending the flexible portion 12c.

The control handle unit 12b is provided with the angle knob 12e and a mode switch (SW) 13a. The mode SW 13a is operated to switch among four modes: a normal mode, a first special mode, and a second special mode, and a simultaneous display mode. In the normal mode, a normal image is displayed on the monitor 18. The first special mode is used to observe a boundary between an atrophic portion (damaged portion) and a normal portion. The atrophic portion refers to a portion, of gastric mucosa (mucous membrane layer of the stomach), with atrophy (shrinkage in linings of stomach) caused by a lesion such as stomach cancer. In the first special mode, a first special image is displayed on the monitor 18. The second special mode is used to observe a difference in color between the atrophic portion and the normal portion. In the second special mode, a second special image is displayed on the monitor 18. The simultaneous display mode is used to observe the boundary between the atrophic portion and the normal portion and the difference in color between the atrophic portion and the normal portion at a time. In the simultaneous display mode, the first and second special images are displayed simultaneously or at a time on the monitor 18.

The processor device 16 is electrically connected to the monitor 18 and the console 19. The monitor 18 outputs and displays image information and the like. The console 19 functions as a UI (user interface), which receives input operation such as setting a function. Note that an external storage unit (not shown) for recording the image information and the like may be connected to the processor device 16.

Figure 2:
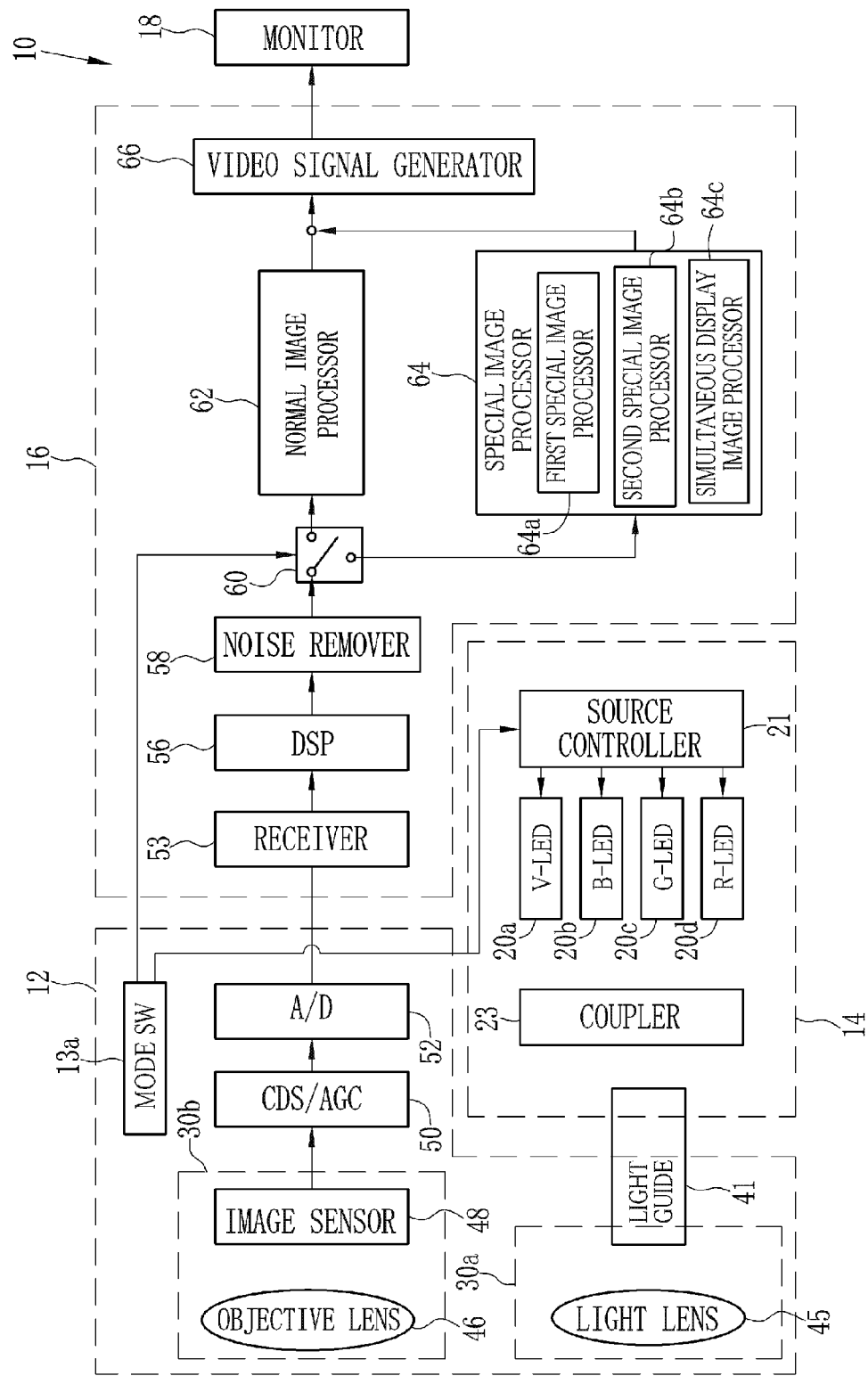
FIG. 2 is a block diagram illustrating functions of the endoscope according to the first embodiment.

As illustrated in FIG. 2, the light source device 14 comprises a V-LED (Violet Light Emitting Diode) 20a, a B-LED (Blue Light Emitting Diode) 20b, a G-LED (Green Light Emitting Diode) 20c, an R-LED (Red Light Emitting Diode) 20d, a source controller 21 for controlling the LEDs 20a to 20d, and a combiner 23. The combiner 23 combines the optical paths of four colors of light from the four colors of LEDs 20a to 20d together. The light combined by the combiner 23 is applied to the object in a body cavity through a light guide (LG) 41 and a light lens 45. The light guide 41 extends inside the insertion section 12a. Note that an LD (Laser Diode) may be used in place of the LED.

Figure 3:
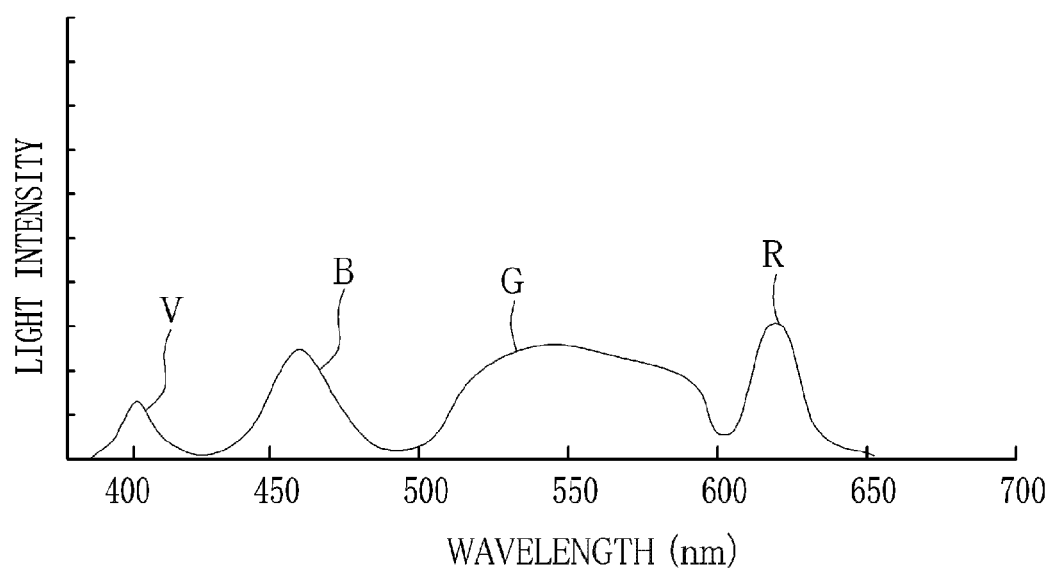
FIG. 3 is a graph illustrating emission spectrums of violet light V, blue light B, green light G, and red light.

As illustrated in FIG. 3, the V-LED 20a generates violet light V having a wavelength range of 380 to 420 nm and the center wavelength 405±10 nm. The B-LED 20b generates blue light B having a wavelength range of 420 to 500 nm and the center wavelength 460±10 nm. The G-LED 20c generates green light G having a wavelength range of 480 to 600 nm. The R-LED 20d generates red light R having a wavelength range of 600 to 650 nm and the center wavelength 620-630 nm.

In each of the normal mode, the first special mode, the second special mode, and the simultaneous display mode, the source controller 21 may turn on the V-LED 20a, the B-LED 20b, the G-LED 20c, and the R-LED 20d. In this case, the mixture of the violet light V, the blue light B, the green light G, and the red light R is applied to the object. In the normal mode, the source controller 21 controls the LEDs 20a to 20d to make a light quantity ratio among the violet light V, the blue light B, the green light G, and the red light R to be Vc:Bc:Gc:Rc. In the first and second special modes and the simultaneous display mode, the source controller 21 controls the LEDs 20a to 20d to make the light quantity ratio among the violet light V, the blue light B, the green light G, and the red light R to be Vs:Bs:Gs:Rs.

As illustrated in FIG. 2, the light guide 41 is incorporated in the endoscope 12 and a universal code that connects the endoscope 12, the light source device 14, and the processor device 16. The light guide 41 transmits the light combined by the combiner 23 to the distal portion 12d of the endoscope 12. Note that a multimode fiber may be used as the light guide 41. For example, a small-diameter fiber cable with the core diameter 105 μm, the clad diameter 125 μm, and the outer diameter φ0.3 to 0.5 mm (including a protection layer, being a jacket) may be used.

The distal portion 12d of the endoscope 12 comprises an illumination optical system 30a and an imaging optical system 30b. The illumination optical system 30a has the light lens 45. The light from the light guide 41 is applied to the object through the light lens 45. The imaging optical system 30b has an objective lens 46 and an image sensor 48. The light reflected from the object is incident on the image sensor 48 through the objective lens 46. Thereby a reflection image of the object is formed on the image sensor 48.

The image sensor 48 is a color image sensor. The image sensor 48 captures the reflection image of the object, and outputs an image signal. It is preferred that the image sensor 48 is a CCD (Charge Coupled Device) image sensor, a CMOS (Complementary Metal-Oxide Semiconductor) image sensor, or the like. The image sensor 48 used in the present invention is a color image sensor for obtaining image signals of three colors, R (red), G (green), and B (blue), that is, a so-called RGB image sensor comprising R pixels with R filters, G pixels with G filters, and B pixels with B filters.

Note that the image sensor 48 may be a so-called complementary color image sensor instead of the RGB image sensor. The complementary color image sensor has complementary color filters of C (cyan), M (magenta), Y (yellow), and G (green). In the case where the complementary color image sensor is used, four colors (CMYG) of image signals are outputted. It is necessary to convert the four colors (CMYG) of image signals into three colors (RGB) of image signals through complementary color/primary color conversion. Alternatively, the image sensor 48 may be a monochrome image sensor with no color filters. In this case, it is necessary that the source controller 21 allows emitting the blue light B, the green light G, and the red light R in a time-division manner. It is also necessary to add a synchronization process in processing the image signals.

The image signal outputted from the image sensor 48 is transmitted to a CDS/AGC circuit 50. The CDS/AGC circuit 50 performs correlated double sampling (CDS) and automatic gain control (AGC) on the image signal, being an analog signal. The image signal which has passed through the CDS/AGC circuit 50 is converted into a digital image signal by an A/D converter 52. The A/D converted digital image signal is inputted to the processor device 16.

The processor device 16 comprises a receiver 53, a DSP (Digital Signal Processor) 56, a noise remover 58, an image processing selector 60, a normal image processor 62, a special image processor 64, and a video signal generator 66. The receiver 53 receives the digital RGB image signals from the endoscope 12. The R image signal corresponds to the signals outputted from the R pixels of the image sensor 48. The G image signal corresponds to the signals outputted from the G pixels of the image sensor 48. The B image signal corresponds to the signals outputted from the B pixels of the image sensor 48.

The DSP 56 performs various types of signal processing (defect correction process, offset processing, gain correction process, linear matrix processing, gamma conversion process, demosaicing process, and the like) on the image signal received. In the defect correction process, signals from defective pixels in the image sensor 48 are corrected. In the offset processing, dark current components are removed from the RGB image signals which have been subjected to the defect correction process. Thereby an accurate zero level is set. In the gain correction process performed after the offset processing, a signal level is adjusted or corrected by multiplying the RGB image signals by a specific gain. After the gain correction process, the RGB image signals are subjected to the linear matrix processing to increase color reproducibility. Thereafter, brightness and saturation are adjusted or corrected through the gamma conversion process. After the linear matrix processing, the RGB image signals are subjected to the demosaicing process (also referred to as equalization process) in which color signal(s) lacking in each pixel is generated by interpolation. Owing to the demosaicing process, each pixel has three colors (RGB) of signals.

The DSP 56 performs gamma correction and the like on the RGB image signals. Thereafter, the noise remover 58 removes noise from the RGB image signals through a noise removing process (for example, moving average method or median filter method). Then, the RGB image signals are transmitted to the image processing selector 60. Note that "input processing unit" of the present invention corresponds to the configuration comprising the receiver 53, the DSP 56, and the noise remover 58.

In the case of the normal mode set by operating the mode SW 13*a*, the image processing selector 60 transmits the RGB image signals to the normal image processor 62. In the case of the first special mode, the second special mode, or the simultaneous display mode, the image processing selector 60 transmits the RGB image signals to the special image processor 64.

The normal image processor 62 performs color conversion process, color enhancement process, and structure enhancement process on the RGB image signals. In the color conversion process, the digital RGB image signals are subjected to 3×3 matrix processing, tone conversion process, three-dimensional LUT process, and the like. Thereby the digital RGB image signals are converted into the color-converted RGB image signals. Next, the color-converted RGB image signals are subjected to various types of color enhancement processes. The color-enhanced RGB image signals are subjected to the structure enhancement process (e.g. spatial frequency enhancement and the like). The structure-enhanced RGB image signals are inputted as the RGB image signals of the normal image from the normal image processor 62 to the video signal generator 66.

The special image processor 64 operates when the mode is set to the first special mode, the second special mode, or the simultaneous display mode. The special image processor 64 comprises a first special image processor 64*a* for producing a first special image, a second special image processor 64*b* for producing a second special image, and a simultaneous display image processor 64*c* for producing a special image used for displaying the first and second special images at a time. The first special image processor 64*a* does not produce the second special image. The second special image processor 64*b* does not produce the first special image. The first special image processor 64*a*, the second special image processor 64*b*, and the simultaneous display image processor 64*c* will be described in detail below. The RGB image signals of the first special image, the second special image, or the special image for simultaneous display, which are generated in the special image processor 64, are inputted to the video signal generator 66.

The video signal generator 66 converts the RGB image signals, which are inputted from the normal image processor 62 or the special image processor 64, into a video signal to be displayed as an image on the monitor 18. Based on the video signal, the monitor 18 displays the normal image, the first special image, or the second special image, or the first and second special images at a time.

Figure 4:
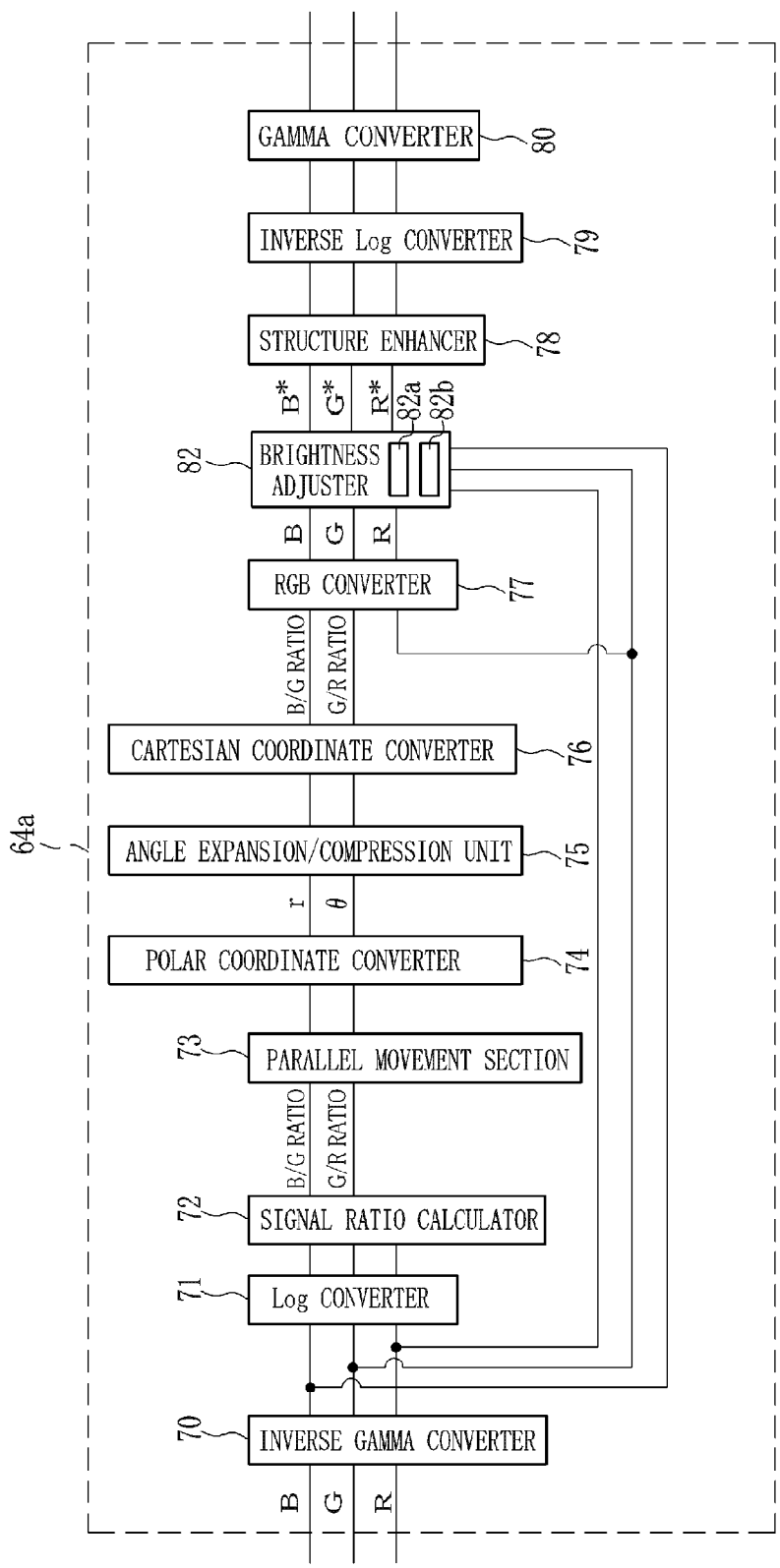
FIG. 4 is a block diagram illustrating functions of a first special image processor.

As illustrated in FIG. 4, the first special image processor 64*a* comprises an inverse gamma converter 70, a log converter 71, a signal ratio calculator 72, a parallel movement section 73, a polar coordinate converter 74, an angle expansion/compression unit 75, a Cartesian coordinate converter 76, an RGB converter 77, a structure enhancer 78, an inverse log converter 79, and a gamma converter 80. The first special image processor 64*a* also comprises a brightness adjuster 82 between the RGB converter 77 and the structure enhancer 78. Note that the "first movement processor" of the present invention corresponds to configuration which includes the parallel movement section 73 and the angle expansion/compression unit 75 in the first special image processor 64*a*.

The inverse gamma converter 70 performs inverse gamma conversion on the inputted RGB channels. The RGB image signals after the inverse gamma conversion are linearly-changing RGB signals which change linearly relative to reflectance from the object. Owing to this, a proportion of the signal components related to various types of biological information increases in the RGB image signals. Note that the linearly-changing R image signal is referred to as a first R image signal. The linearly-changing G image signal is referred to as a first G image signal. The linearly-changing B image signal is referred to as a first B image signal.

The log converter 71 performs log conversion of each of the first RGB image signals (which correspond to "first color image signal" of the present invention). Thereby, log-converted R image signal (log R), log-converted G image signal (log G), and log-converted B image signal (log B) are obtained. The signal ratio calculator 72 (which corresponds to a "color information obtaining section" of the present invention) performs difference processing (log G−log B=log G/B=−log(B/G)) based on the log-converted G image signal and the log-converted B image signal. Thereby, the B/G ratio is calculated. The B/G ratio refers to −log(B/G) with the "−log" omitted. The G/R ratio is calculated by difference processing (log R−log G=log R/G=−log(G/R)) based on the log-converted R image signal and the log-converted G image signal. The G/R ratio refers to −log(G/R) with the "−log" omitted in a manner similar to the B/G ratio.

Note that the B/G ratio and the G/R ratio are calculated with respect to the pixels in the same positions in the B image signal, the G image signal, and the R image signal. The B/G ratio and the G/R ratio are calculated for each pixel. The B/G ratio correlates with a blood vessel depth (distance between the mucosal surface and a position of a specific blood vessel), so that the B/G ratio varies with the blood vessel depth. The G/R ratio correlates with the blood volume (hemoglobin index), so that the G/R ratio varies with the blood volume.

The parallel movement section 73 performs the first process for the signal ratio space. In the first process, the parallel movement section 73 translates or moves the coordinates in a parallel manner from a certain area or range, based on the B/G and G/R ratios calculated by the signal ratio calculator 72. The polar coordinate converter 74 performs the conversion into the radial coordinate r and the angular coordinate θ based on the B/G and G/R ratios (coordinates) which have been moved in the parallel manner by the parallel movement section 73. The polar coordinate converter 74 performs the conversion into the radial coordinate r and the angular coordinate θ for each pixel. The angle expansion/compression unit 75 performs a second process (for the signal ratio space). In the second process, the angle expansion/compression unit 75 expands or compresses the angular coordinate θ based on the radial coordinate r and the angular coordinate θ which have been subjected to the first process (for the signal ratio space) and the polar coordinate conversion performed by the polar coordinate converter 74. The first and second processes (for the signal ratio space) will be described below in detail.

The Cartesian coordinate converter 76 converts the expanded or compressed radial coordinate r and angular coordinate θ (the radial coordinate r and angular coordinate θ which have been subjected to the second process for the signal ratio space by the angle expansion/compression unit 75), into Cartesian coordinates. Thereby the radial coordinate r and angular coordinate θ are converted back into the B/G ratio and the G/R ratio. The RGB converter 77 (which corresponds to a "color image signal converter" of the present invention) uses at least one of the first RGB image signals, which are outputted from the inverse gamma converter 70, to convert the B/G and G/R ratios, which have passed through the Cartesian coordinate converter 76, into the second RGB image signals (which correspond to "second color image signals" of the present invention). To convert the B/G ratio into a second B image signal, the RGB converter 77 performs arithmetic operations based on the B/G ratio and the first G image signal of the first RGB image signals, for example. To convert the G/R ratio into a second R image signal, the RGB converter 77 performs arithmetic operations based on the G/R ratio and the first G image signal of the first RGB image signals, for example. The RGB converter 77 outputs the first G image signal as a second G image signal, without any conversion.

The brightness adjuster 82 adjusts or corrects the pixel values of the second RGB image signals based on the first RGB image signals and the second RGB image signals. A reason for adjusting the pixel values of the second RGB image signals by the brightness adjuster 82 is as follows. The brightness of the second RGB image signals, which are obtained by the expansion and compression processes of the color region performed by the parallel movement section 73 and the angle expansion/compression unit 75, may become significantly different from the brightness of the first RGB image signals. The brightness adjuster 82 adjusts the pixel values of the second RGB image signals to make the brightness of the second RGB image signals after the brightness adjustment equal to the brightness of the first RGB image signals.

The brightness adjuster 82 comprises a first brightness information calculator 82a and a second brightness information calculator 82b. The first brightness information calculator 82a calculates first brightness information Yin based on the first RGB image signals. The second brightness information calculator 82b calculates second brightness information Yout based on the second RGB image signals. The first brightness information calculator 82a calculates the first brightness information Yin with the use of an arithmetic expression "kr×pixel value of first R image signal+kg×pixel value of first G image signal+kb×pixel value of first B image signal". The second brightness information calculator 82b calculates the second brightness information Yout with the use of an arithmetic expression similar to that described above, in a manner similar to the first brightness information calculator 82a. After calculating the first brightness information Yin and the second brightness information Yout, the brightness adjuster 82 performs arithmetic operations based on the following expressions (E1) to (E3), thereby adjusting the pixel values of the second RGB image signals.

$R^* =$ pixel value of second $R$ image signal$\times Yin/Yout$ (E1)

$G^* =$ pixel value of second $G$ image signal$\times Yin/Yout$ (E2)

$B^* =$ pixel value of second $B$ image signal$\times Yin/Yout$ (E3)

Note that "R*" denotes the second R image signal after the brightness adjustment. "G*" denotes the second G image signal after the brightness adjustment. "B*" denotes the second B image signal after the brightness adjustment. Each of "kr", "kg", and "kb" is an arbitrary constant within a range from 0 to 1.

The structure enhancer 78 performs the structure enhancement process on the second RGB image signals after the brightness adjustment in the brightness adjuster 82. The structure enhancement process may be frequency filtering or the like. The inverse log converter 79 performs inverse log conversion on the second RGB image signals which have passed through the structure enhancer 78. Thereby the second RGB image signals with antilogarithmic pixel values are obtained. The gamma converter 80 performs the gamma conversion on the RGB image signals which have passed through the inverse log converter 79. Thereby the second RGB image signals with the tone suitable for an output device (e.g. the monitor 18) are obtained. The RGB image signals, which have passed through the gamma converter 80, are transmitted as the RGB image signals of the first special image to the simultaneous display image processor 64c or the video signal generator 66.

Figure 5:
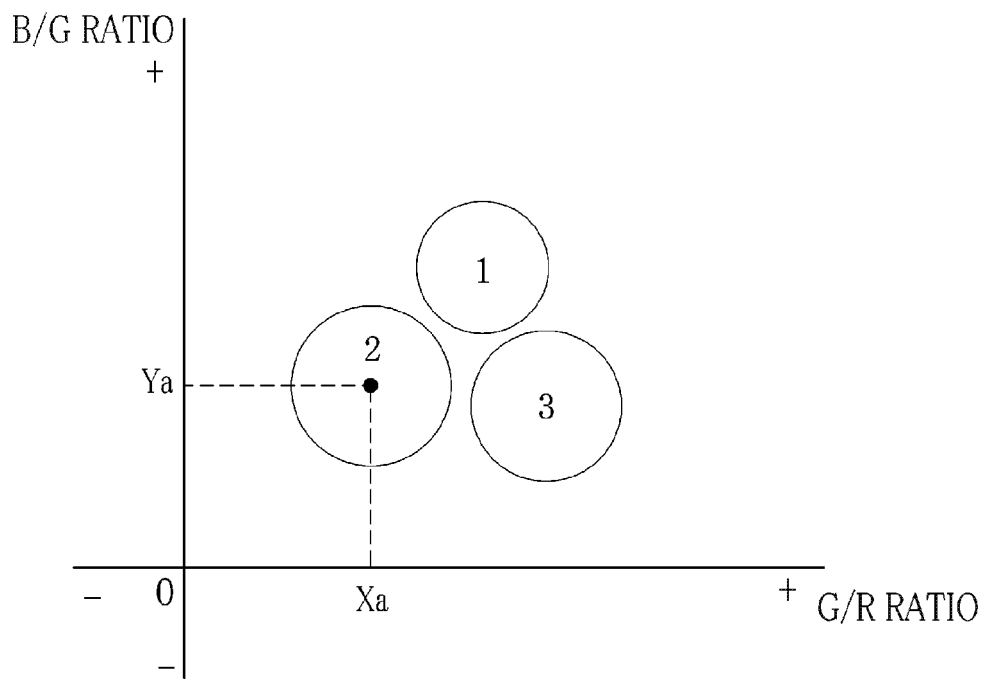
FIG. 5 is an explanatory view illustrating a first process for a signal ratio space.
Figure 6:
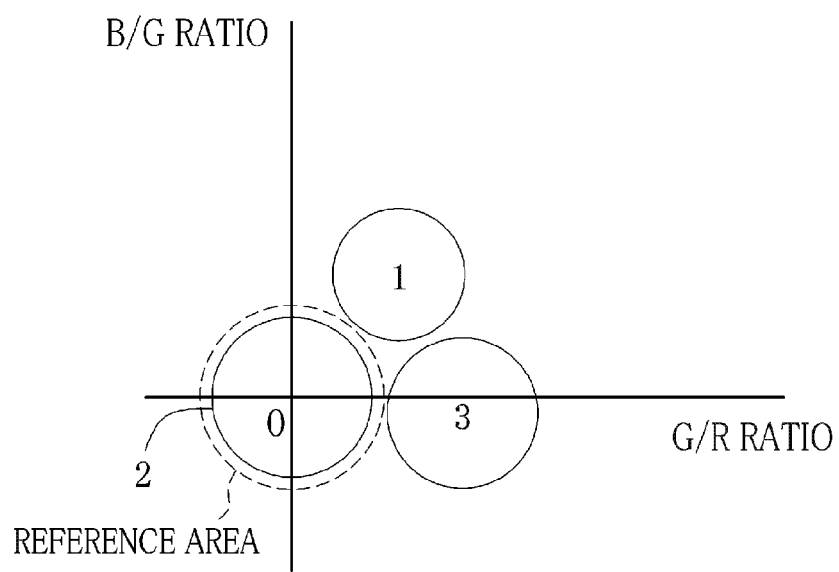
FIG. 6 is a graph illustrating distribution of the first to third observation areas after the first process for the signal ratio space.

As illustrated in FIG. 5, the first process (for the signal ratio space) performed by the parallel movement section 73 will be described below using a feature space (signal ratio space), being a two-dimensional color space formed by the B/G ratio (vertical axis) and the G/R ratio (horizontal axis). In the first process (for the signal ratio space), first, an average value (Xa, Ya) of the coordinates in a second observation area, in which atrophic mucosa damaged or shrunk by atrophic gastritis is distributed, in the signal ratio space is calculated. Next, all of the coordinates corresponding to the second observation area, all of the coordinates corresponding to a first observation area, in which the normal mucosa is distributed, and all of the coordinates corresponding to a third observation area, which is located beneath the atrophic mucosa damaged or shrunk by the atrophic gastritis and in which deep blood vessels seen through the atrophic mucosa are distributed, are moved in a parallel manner by the magnitude of the average value (Xa, Ya) in the negative direction with respect to the vertical direction and in the negative direction with respect to the horizontal direction. Thereby, as illustrated in FIG. 6, the coordinates corresponding to the second observation area move to the reference area that contains the origin point of the signal ratio space, and the coordinates corresponding to the first and third observation areas move toward the reference area while the positional relationship with the coordinates corresponding to the second observation area is maintained. The reference area refers to a region with low saturation, which excludes the first and third observation areas which have been subjected to the first process (for the signal ratio space).

Figure 7:
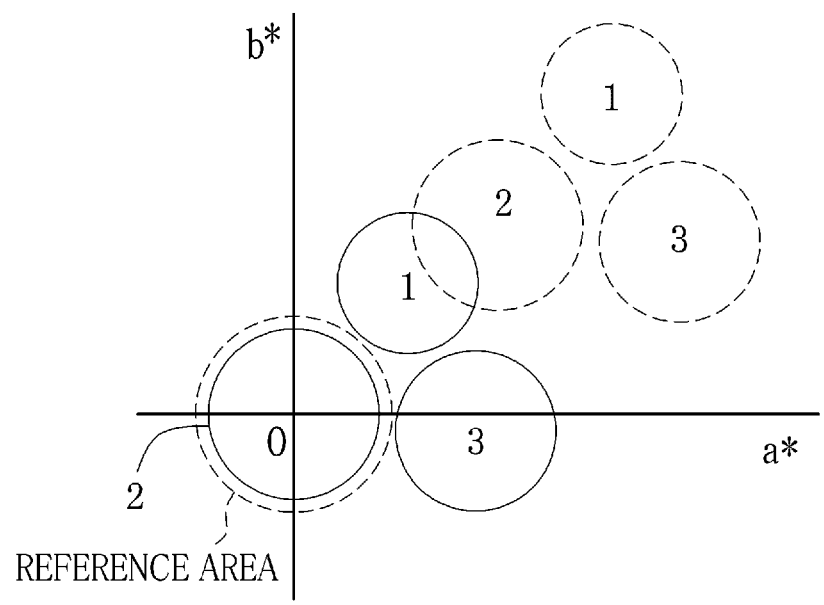
FIG. 7 is a graph illustrating distribution of the first to third observation areas after the first process of a case where the feature space is ab space.
Figure 8:
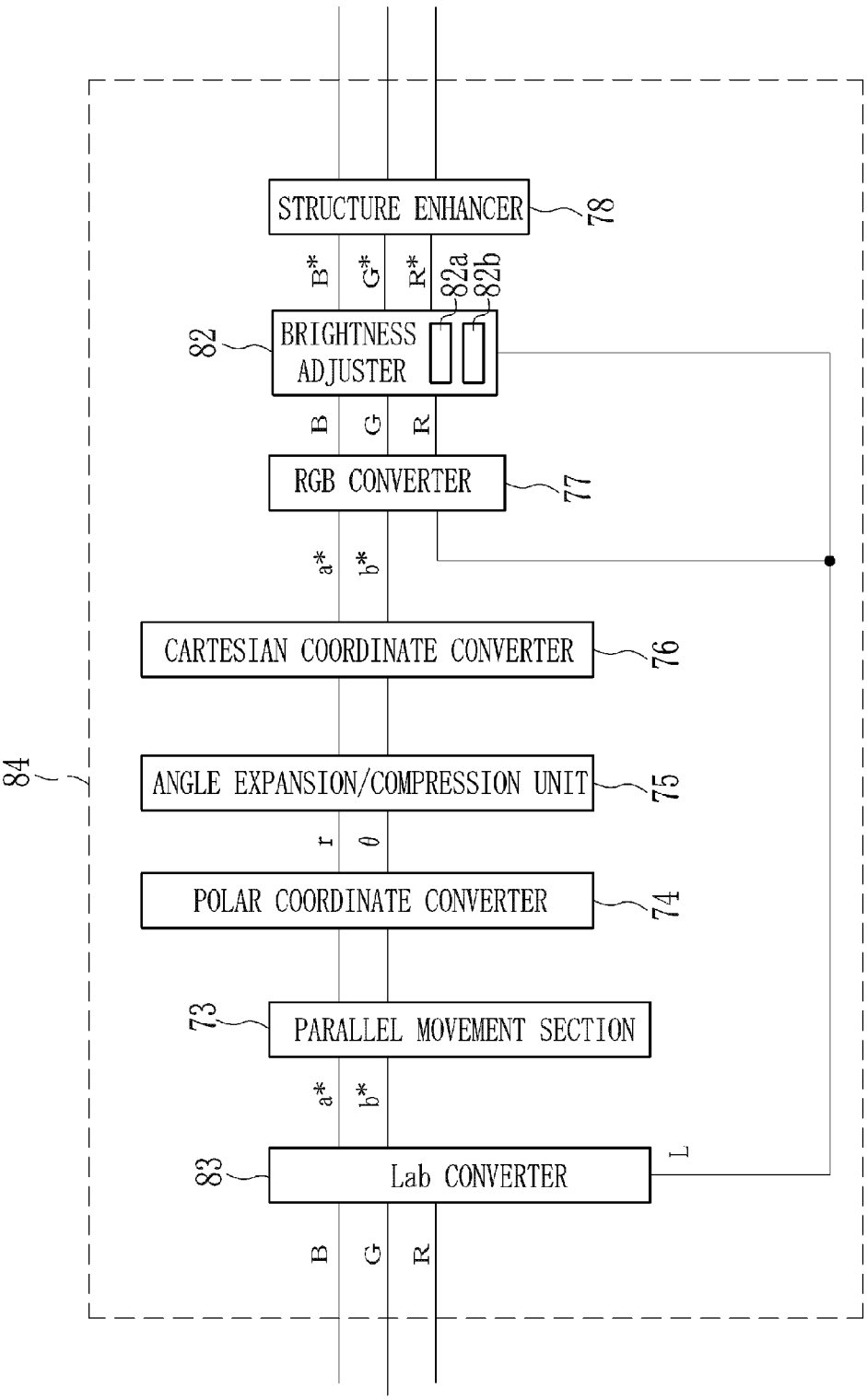
FIG. 8 is a block diagram illustrating functions of the special image processor used for the ab space.

Note that in the case of the feature space (ab space) formed by a* and b* (color components a* and b*, being the color information, in a CIE Lab space, the same hereinafter), which are obtained by the Lab conversion of the first RGB image signals performed by a Lab converter (which corresponds to the "color information obtaining section" of the present invention) 83 (see FIG. 8), all of the coordinates corresponding to the first observation area, all of the coordinates corresponding to the second observation area, and all of the coordinates corresponding to the third observation areas are moved in a parallel manner by the average value of the coordinates which correspond to the second observation area so that the coordinates which correspond to the second observation area are moved to the reference area (see FIG. 7). Here, in FIG. 7, "the first to third observation areas depicted with dotted lines" represent the positions of the first to third observation areas in the ab space before the first process (for the ab space). "The first to third observation areas depicted with solid lines" represent the positions of the first to third observation areas in the ab space after the first process.

Note that, in the case where the first process (for the ab space) is performed with the use of a* and b*, a special image processor 84 (see FIG. 8) is used. Unlike the special image processor 64a, the special image processor 84 is not provided with the inverse gamma converter 70, the log converter 71, the signal ratio calculator 72, the inverse log converter 79, and the gamma converter 80. Instead, the special image processor 84 comprises the Lab converter 83, which corresponds to the "color information obtaining section" of the present invention. The components, other than those described above, of the special image processor 84 are the same as or similar to the components of the special image processor 64a.

The Lab converter 83 converts the first RGB image signals into L, a*, and b* through the well-known Lab conversion. The "L" is transmitted to the RGB converter 77 and the brightness adjuster 82. The "a*" and "b*" are transmitted to the polar coordinate converter 74. The RGB converter 77 converts the "a*" and which have passed through the Cartesian coordinate converter 76, and the "L" into the second RGB image signals. The first brightness information calculator 82a of the brightness adjuster 82 converts the "L", which is transmitted from the Lab converter 83, into a luminance signal Y with the use of a predetermined conversion equation. The converted luminance signal Y is referred to as the first brightness information Yin. The second brightness information calculator 82b calculates the second brightness information Yout from the second RGB image signals. The brightness adjuster 82 uses the first brightness information Yin and the second brightness information Yout to adjust the pixel values of the second RGB image signals. Note that the method for calculating the second brightness information Yout and the method for adjusting the pixel values of the second RGB image signals are the same as or similar to those of the special image processor 64a.

Figure 9:
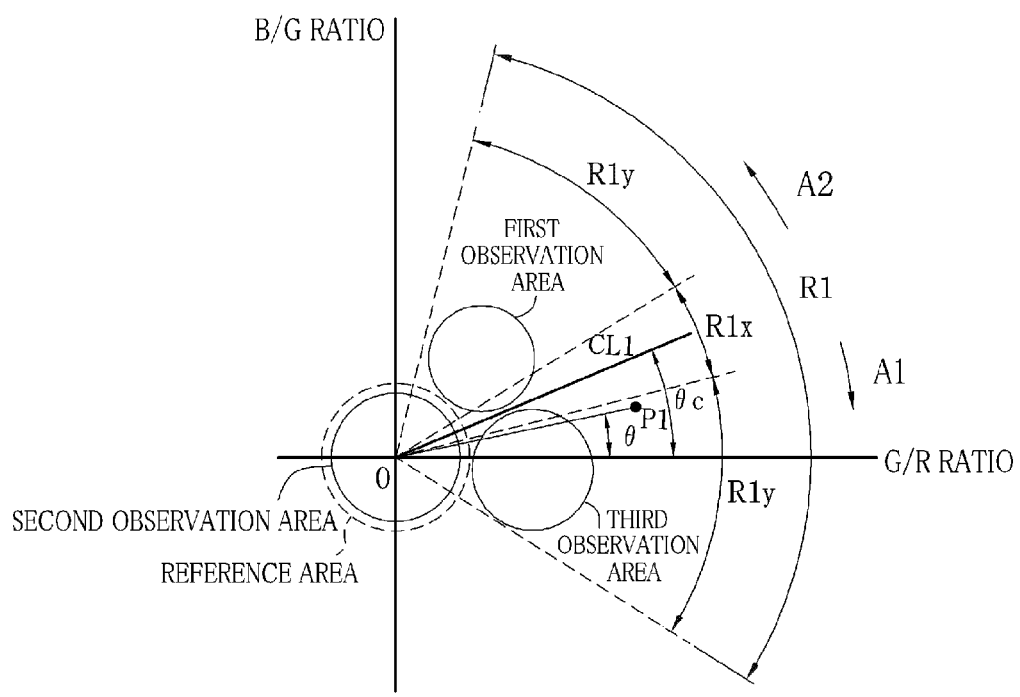
FIG. 9 is an explanatory view illustrating a second process for the signal ratio space.

As illustrated in FIG. 9, in the second process (for the signal ratio space) performed by the angle expansion/compression unit 75, the angle θ of the coordinates (point) P1 in an angle changing region R1 is changed while the angle θ of the coordinates (point) outside the angle changing region R1 is not changed. The angle changing region R1 is set to include the first observation area and the third observation area. Note that, in the second process (for the signal ratio space), the radial coordinate r of the coordinates (point) inside the angle changing region R1 is not changed.

Figure 10:
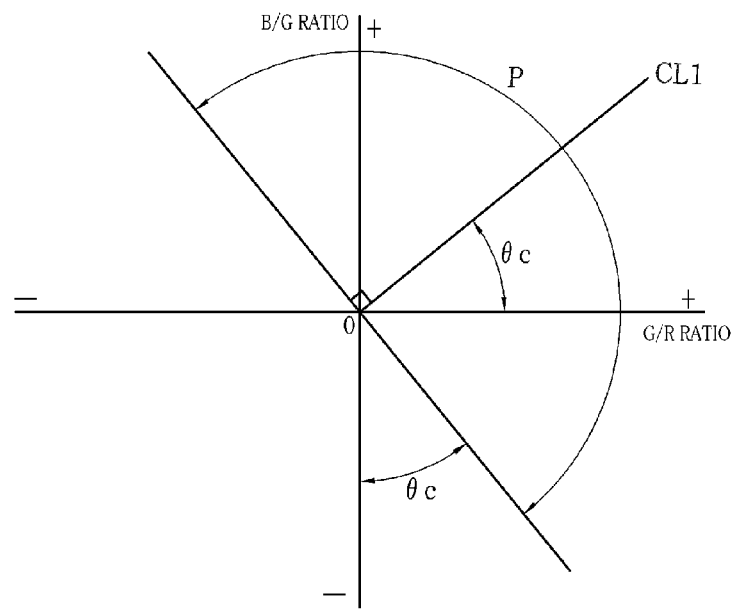
FIG. 10 is a graph illustrating a region to which the angle θ in the angle changing region R1 is moved.

In the angle changing region R1, a first center line CL1 is set between the first observation area and the third observation area. The first center line CL1 has an angle θc. The coordinates (point) with an angle (angular coordinate) θ which is smaller than the angle θc in the angle changing region R1 are rotated in the clockwise direction A1 while the coordinates (point) with an angle (angular coordinate) θ which is greater than the angle θc in the angle changing region R1 are rotated in the counter clockwise direction A2. Note that, in the case where the angle θ is within a range R1x extending from the first center line CL1, it is preferred to perform the expansion process for changing the angle θ at an angle change rate Wx, which is greater than "1". In the case where the angle θ is within a range R1y outside the range R1x, it is preferred to perform the compression process for changing the angle θ at an angle change rate Wy, which is less than "1". It is preferred to move the coordinates, which are located in the angle changing region R1, within a region extending ±90° (degrees) from the first center line CL1 (e.g. a region P extending from "270°+θc" to "θc+90°" in the case where the "positive" horizontal axis is 0° and an angle is expressed in degree from 0° to 360° (see FIG. 10)) through the second process (for the signal ratio space). Note that in a case where the angle change rate is "1", the angle θ does not change when subjected to the process for changing the angle θ.

Here, an angle change rate is represented by the inclination of a straight line "L1", being the tangent line of a curve CV1. The curve CV1 depicts the relationship between angles θ and Eθ. The inclination of the straight line L1 is greater than "1" in the range R1x. On the other hand, the inclination of the straight line L1 is less than "1" in the range R1y (see FIG. 11). The inclination of the straight line L1 outside the angle changing region R1 is "1" (see FIG. 11).

Figure 11:
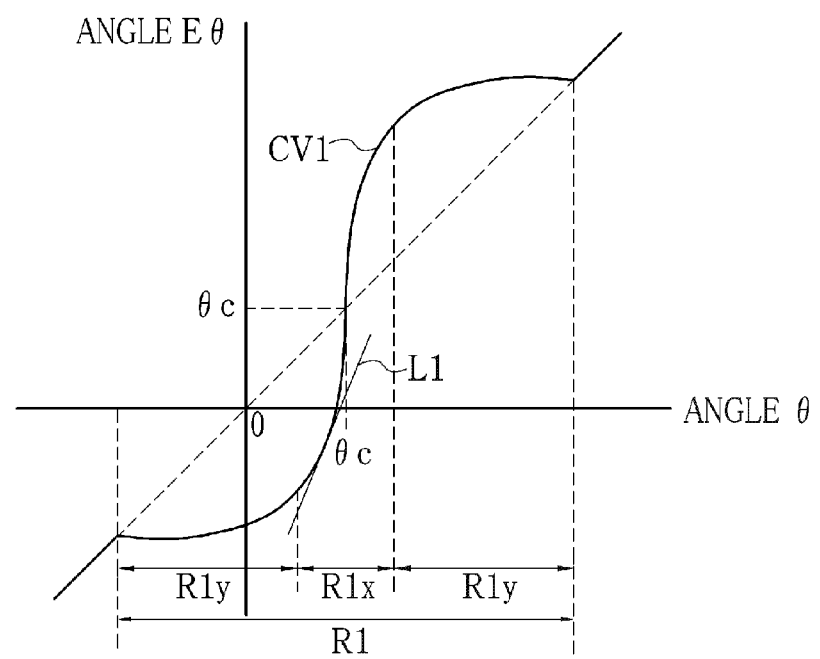
FIG. 11 is a graph representing a relationship between the angle θ and the angle Eθ which is obtained after the second process (for the signal ratio space)

By the second process (for the signal ratio space), as illustrated in FIG. 11, the angle θ which is less than the angle θc in the angle changing region R1 is changed to an angle Eθ which is smaller than the angle θ. The angle θ greater than the angle θc is changed to the angle Eθ which is greater than the angle θ. The angle θ outside the angle changing region R1 is changed to the angle Eθ which is equivalent to the angle θ (identical transformation).

Figure 12:
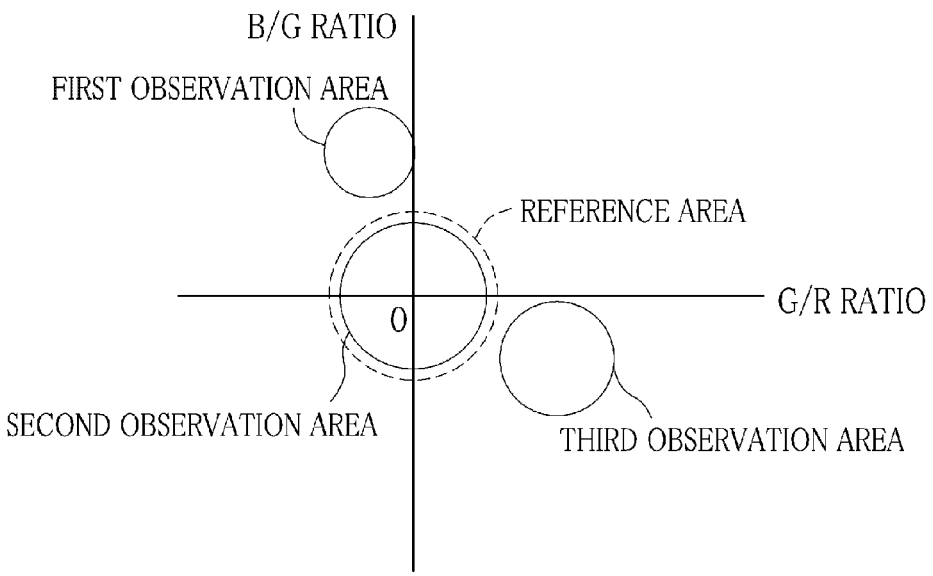
FIG. 12 is a graph illustrating distribution of the first to third observation areas after the second process for the signal ratio space.

Thereby, as illustrated in FIG. 12, most of the coordinates corresponding to the first observation area are moved to the second quadrant of the signal ratio space and most of the coordinates corresponding to the third observation area are moved to the fourth quadrant of the signal ratio space while the coordinates corresponding to the second observation area are maintained in the reference area. Thus, the coordinates corresponding to the first observation area and the coordinates corresponding to the third observation area are located in the different quadrants in the signal ratio space. The first special image obtained after the second process (for the signal ratio space) clearly shows the boundary between the atrophic portion, which includes atrophic mucosa and the deep blood vessels seen through the atrophic mucosa, and the normal portion with the normal mucosa.

Figure 13:
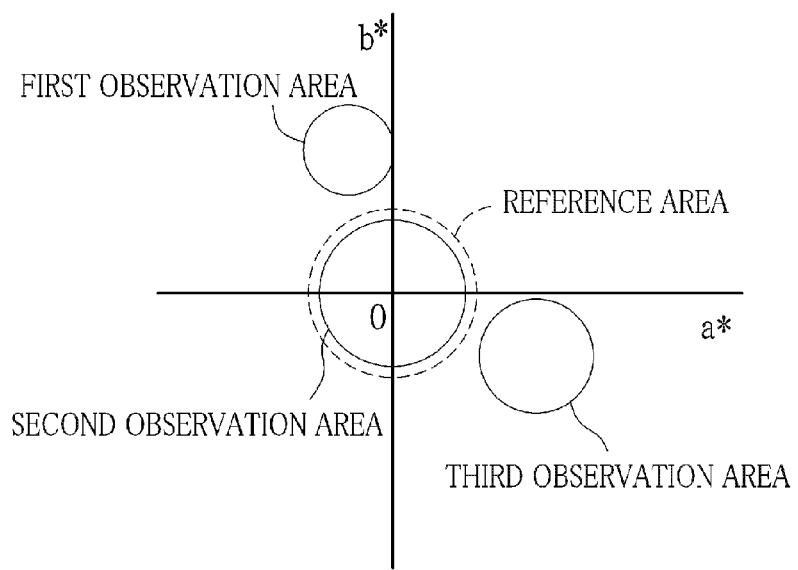
FIG. 13 is a graph illustrating distribution of the first to third observation areas after the second process for the ab space.

Note that in the case where the feature space is the ab space, as illustrated in FIG. 13, the second process (for the ab space) moves most of the coordinates which correspond to the first observation area to the second quadrant of the ab space and most of the coordinates which correspond to the third observation area to the fourth quadrant of the ab space while the coordinates which correspond to the second observation area are maintained within the reference area. It is preferred that the brightness adjuster 82 adjusts the pixel values of the second RGB image signals obtained after the first and second processes (for the ab space). The method for adjusting the second RGB image signals is the same as or similar to that described above.

Figure 14:
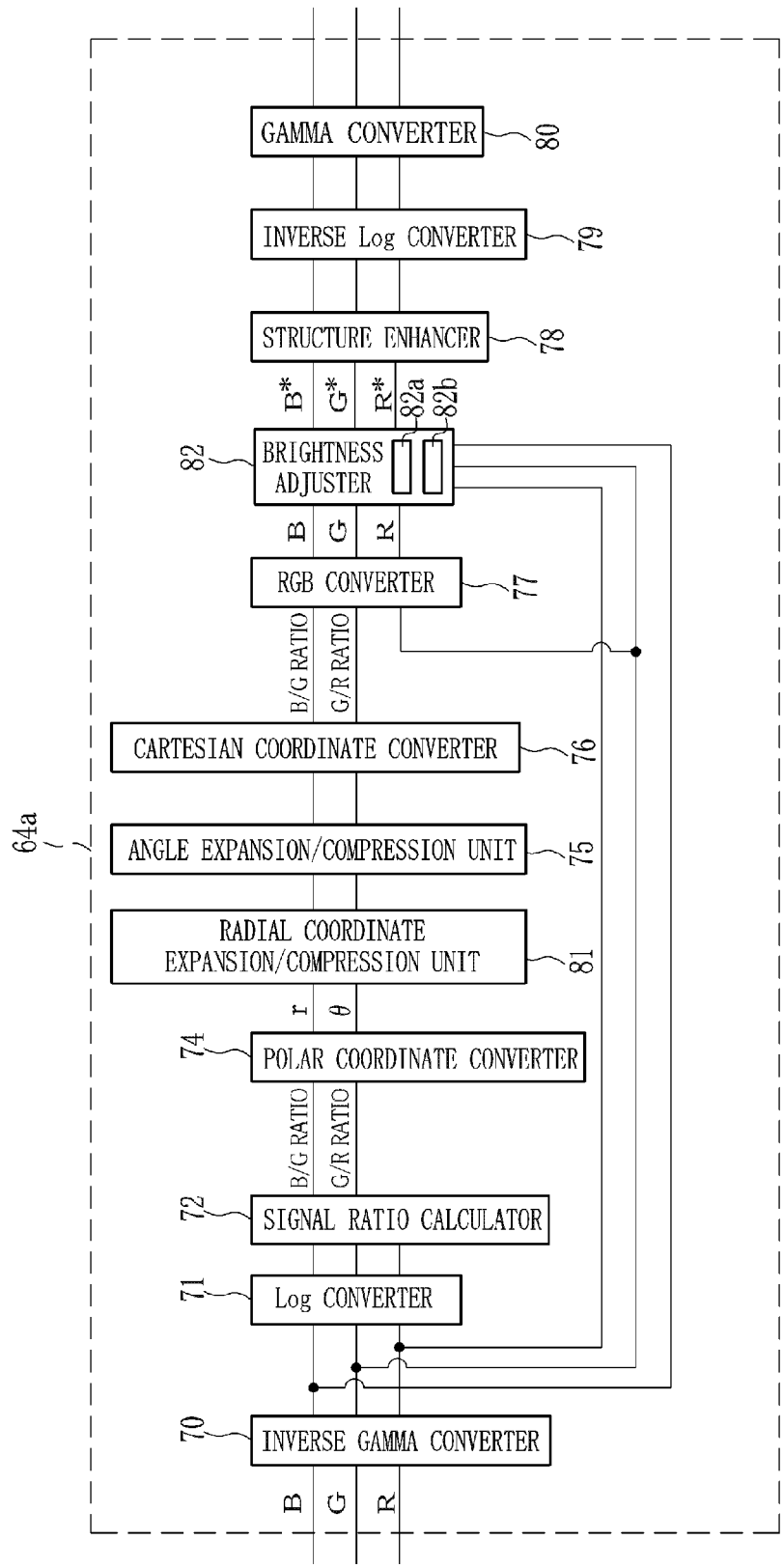
FIG. 14 is a block diagram illustrating functions of the second special image processor.

As illustrated in FIG. 14, the second special image processor 64b has the same or similar configuration as that of the first special image processor 64a. However, the second special image processor 64b is provided with the radial coordinate expansion/compression unit 81 in place of the parallel movement section 73. The process performed by the angle expansion/compression unit 75 in the second special image processor 64b differs from the second process (for the signal ratio space) performed by the first special image processor 64a. Note that the "second movement processor" of the present invention corresponds to the configuration which includes the radial coordinate expansion/compression unit 81 and the angle expansion/compression unit 75.

Figure 15:
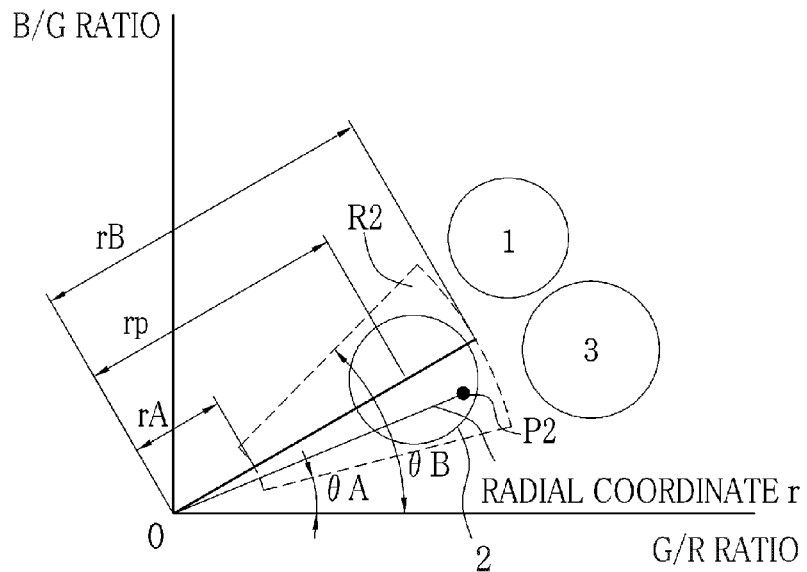
FIG. 15 is an explanatory view illustrating a third process for the signal ratio space.

The radial coordinate expansion/compression unit 81 performs the third process (for the signal ratio space), in which the radial coordinate r is changed based on the radial coordinate r and the angle θ, which have been converted by the polar coordinate converter 74. Referring to FIG. 15, the third process is described using the signal ratio space. In the third process, a radial coordinate r of the coordinates (point) P2 located within the radial coordinate changing region R2 is changed while a radial coordinate r of the coordinates (point) located outside of the radial coordinate changing region R2 is not changed. In the radial coordinate changing region R2, the radial coordinate r takes a value between "rA" and "rB" and the angle θ takes a value between "θA" and "θB" (rA<rB, θA<θB). The radial coordinate changing region R2 is set to include the second observation area, in which atrophic mucosa (damaged mucosal tissue) caused by the atrophic gastritis (damaged stomach lining) is distributed, and exclude the first observation area and the third observation area. In the first observation area, normal mucosa is distributed. The third observation area is located beneath the atrophic mucosa caused by the atrophic gastritis, and deep blood vessels are distributed in the third observation area. The deep blood vessels in the third observation area appear through the atrophic mucosa as the atrophy progresses.

Note that, in the third process for the signal ratio space, the angular coordinate (angle) θ of the coordinates (point) in the radial coordinate changing region R2 is not changed. In the third process, it is preferred to perform an expansion process on the radial coordinate r in the case where the radial coordinate r is in a range of "rp" to "rB" and a compression process on the radial coordinate r in the case where the radial coordinate r is in a range of "rA" to "rp". In the expansion process, the radial coordinate r is changed at a radial coordinate change ratio Vx, which is greater than "1". In the compression process, the radial coordinate r is changed at a radial coordinate change ratio Vy, which is less than 1. Note that, in the case where the radial coordinate change ratio is "1", the length of the radial coordinate r does not change even if the process for changing the radial coordinate r is performed.

Here, a radial coordinate change rate is represented by the inclination of a straight line "L2", being the tangent line of a curve CV2. The curve CV2 depicts the relationship between the radial coordinate r and the radial coordinate Er. The inclination of the straight line L2 is greater than "1" in the range of "rp" to "rB". On the other hand, the inclination of the straight line L2 is less than "1" in the range of "rA" to "rp" (see FIG. 16). The inclination of the straight line L2 outside the radial coordinate changing region R2 is "1" (see FIG. 16).

Figure 16:
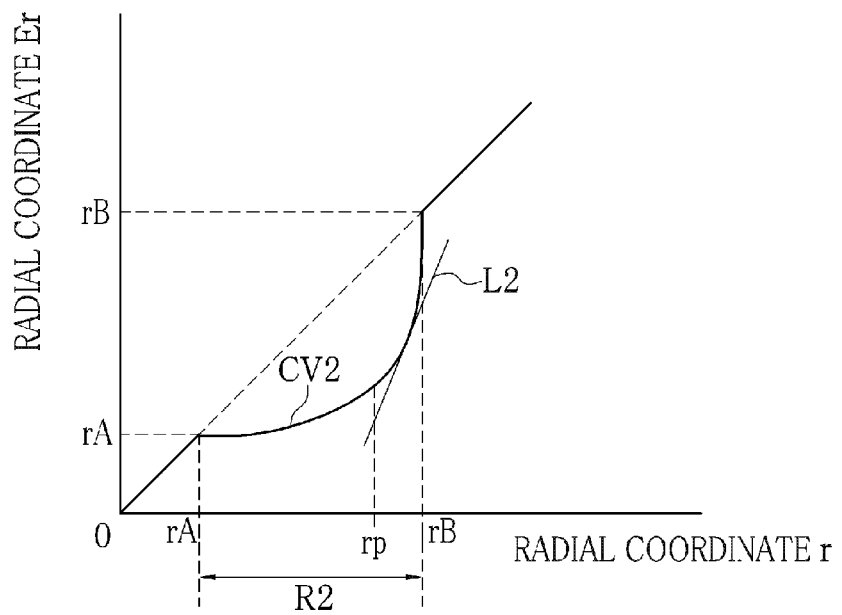
FIG. 16 is a graph illustrating a relationship between radial coordinate r and radial coordinate Er.
Figure 17:
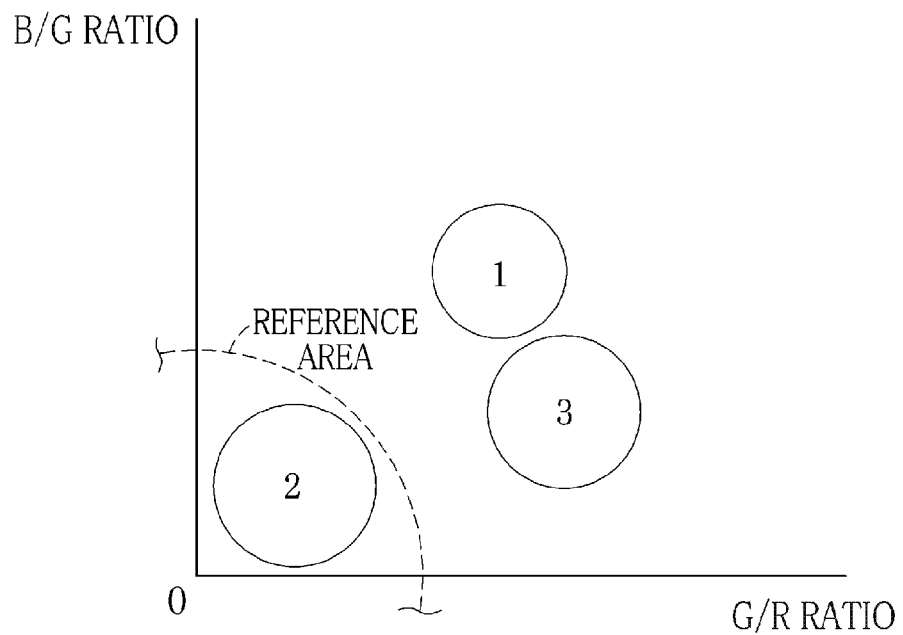
FIG. 17 is a graph illustrating distribution of the first to third observation areas after a third process for the signal ratio space.

By the third process (for the signal ratio space), as illustrated in FIG. 16, the radial coordinate r in the radial coordinate changing region R1 is changed to the radial coordinate Er which is smaller than the radial coordinate r. The radial coordinate r located outside the radial coordinate changing region R2 is changed to the radial coordinate Er which is equivalent to the radial coordinate r (identical transformation). Thereby, as illustrated in FIG. 17, only the coordinates which correspond to the second observation area are moved to the reference area that contains the origin point while the coordinates which correspond to the first observation area and the coordinates which correspond to the third observation area are maintained unchanged. Note that the saturation in the special image is decreased by moving the coordinates which correspond to the second observation area.

Figure 18:
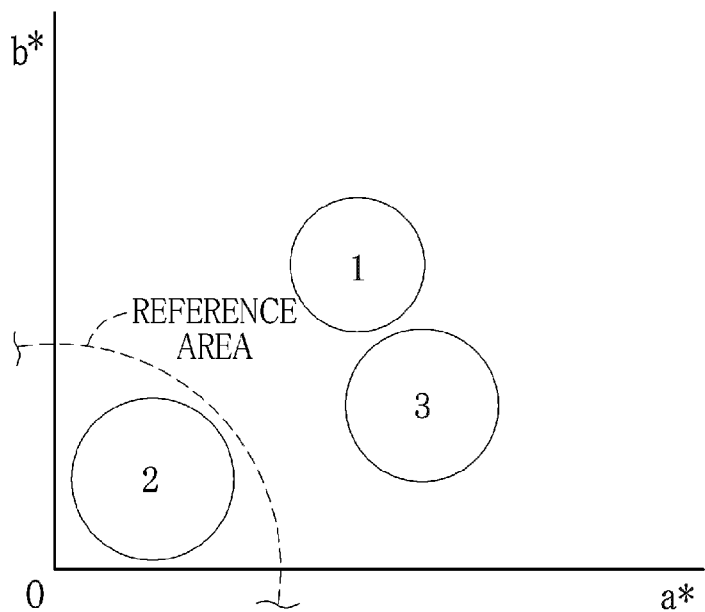
FIG. 18 is a graph illustration distribution of the first to third observation areas after the third process for the ab space.

Note that, in the case where the feature space is the ab space, as illustrated in FIG. 18, the third process (for the ab space) moves only the coordinates which correspond to the second observation area to the reference area that contains the origin point while the coordinates which correspond to the first observation area and the coordinates which correspond to the third observation area are maintained unchanged.

Figure 19:
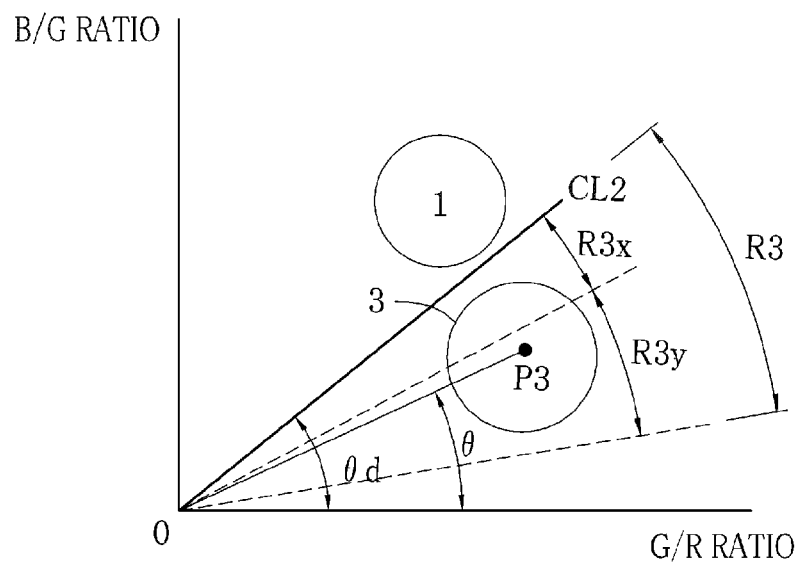
FIG. 19 is an explanatory view illustrating a fourth process for the signal ratio space.

The angle expansion/compression unit 75 of the second special image processor 64b performs a fourth process (for the signal ratio space). In the third process, the angle expansion/compression unit 75 changes the angle θ based on the radial coordinate r and the angle θ which are obtained after the third process (for the signal ratio space), to move the coordinates which correspond to the third observation area while the coordinates which correspond to the first observation area are maintained unchanged. In the fourth process (for the signal ratio space), as illustrated in FIG. 19, the angle θ of coordinates (point) P3 within the angle changing region R3 is changed while the angle θ of coordinates outside the angle changing region R3 is not changed. The angle changing region R3 is set to include the third observation area and exclude the first observation area. Note that in the fourth process (for the signal ratio space), the radial coordinate r of the coordinates in the angle changing region R3 is not changed.

Figure 20:
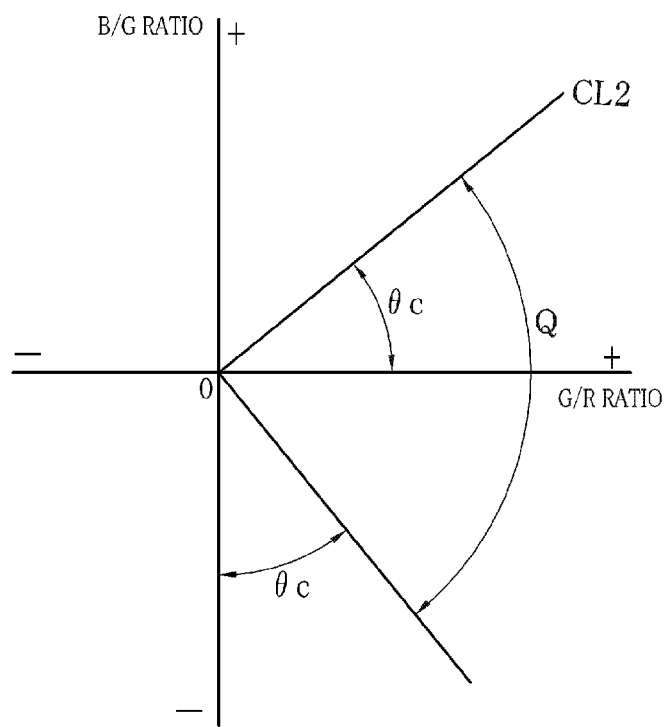
FIG. 20 is a graph illustrating a region to which an angle θ in an angle changing region R3 is moved.

A second center line CL2 is set between the first observation area and the third observation area in the angle changing region R3. The second center line CL2 is set at an angle θd. The coordinates having the angle θ which is less than or equal to the angle θd in the angle changing region R3 are rotated in the clockwise direction. Note that, in the case where the angle θ is within a range R3x extending from the second center line CL2, it is preferred to perform the expansion process for changing the angle θ at an angle change rate Wx, which is greater than "1". In the case where the angle θ is within a range R3y outside the range R3x, it is preferred to perform the compression process for changing the angle θ at an angle change rate Wy, which is less than "1". It is preferred to move the coordinates, which are located in the angle changing region R3, within a region extending −90° (degrees) from the second center line CL2 (e.g. a region Q extending from "270°+θd" to "θd" in the case where the "positive" horizontal axis is 0° and an angle is expressed in degree from 0° to 360° (see FIG. 20)) through the fourth process (for the signal ratio space). Note that in a case where the angle change rate is "1", the angle θ does not change when subjected to the process for changing the angle θ.

Here, an angle change rate is represented by the inclination of a straight line "L3", being the tangent line of a curve CV3. The curve CV3 depicts the relationship between angles θ and Eθ. The inclination of the straight line L3 is greater than "1" in the range R3x. On the other hand, the inclination of the straight line L3 is less than "1" in the range R3y (see FIG. 21). The inclination of the straight line L3 outside the angle changing region R3 is "1" (see FIG. 21).

Figure 21:
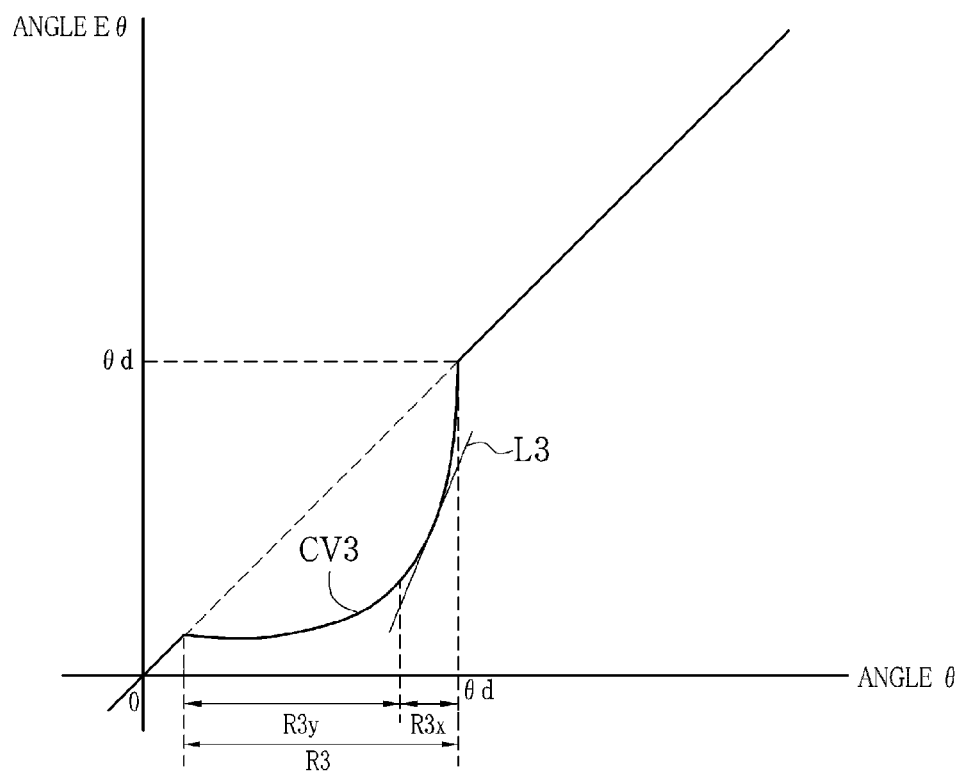
FIG. 21 is a graph illustrating a relationship between angle θ and angle Eθ obtained after a fourth process for the signal ratio space.

By the fourth process (for the signal ratio space), as illustrated in FIG. 21, the angle θ which is located in the angle changing region R3 is changed to the angle Eθ which is smaller than the angle θ. The angle θ outside the angle changing region R3 is changed to the angle Eθ which is equivalent to the angle θ (identical transformation).

Figure 22:
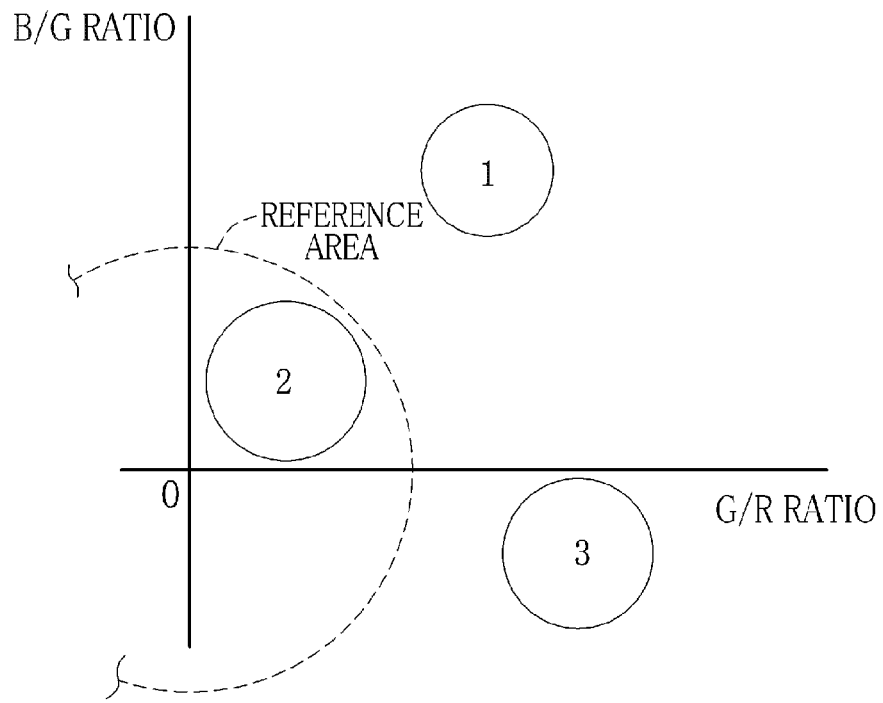
FIG. 22 is a graph illustrating distribution of the first to third observation areas after the fourth process for the signal ratio space.

Thereby, as illustrated in FIG. 22, most of the coordinates corresponding to the third observation area are moved to the fourth quadrant of the signal ratio space while the coordinates corresponding to the second observation area are maintained in the reference area and while the coordinates corresponding to the first observation area are maintained unchanged. By moving the coordinates which correspond to the third observation area from the first quadrant to the fourth quadrant, the hue is changed in the signal ratio space. Thus, the coordinates corresponding to the first observation area, the coordinates corresponding to the second observation area, and the coordinates corresponding to the third observation area are moved away from each other.

Figure 23:
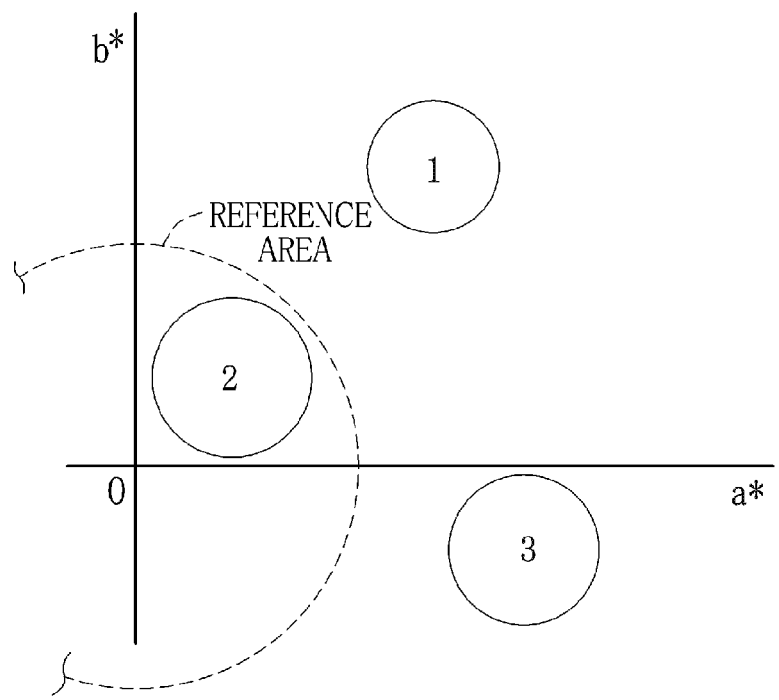
FIG. 23 is a graph illustrating distribution of the first to third observation areas after the fourth process for the ab space.

Note that, as illustrated in FIG. 23, in the case where the feature space is the ab space, most of the coordinates corresponding to the third observation area are moved to the fourth quadrant of the ab space by the fourth process (for the ab space) while the coordinates corresponding to the second observation area are maintained in the reference area and while the coordinates corresponding to the first observation area are maintained unchanged. It is preferred that the brightness adjuster 82 adjusts the pixel values of the second RGB image signals obtained after the third and fourth processes (for the ab space). The method for adjusting the pixel values of the second RGB image signals is the same or similar to that described above.

In the second special image obtained after the fourth process (for the signal ratio space), the color of the normal portion is maintained in the display while the color of the atrophic mucosa of the atrophic portion with the atrophic gastritis is displayed in faded colors and the deep blood vessels seen through the atrophic mucosa are displayed in a color which corresponds to the atrophic state. Thus, the second special image displayed shows the gastric mucosa infected with atrophic gastritis in actual colors, so that the difference in color between the normal portion and the atrophic portion is clear.

Figure 24:
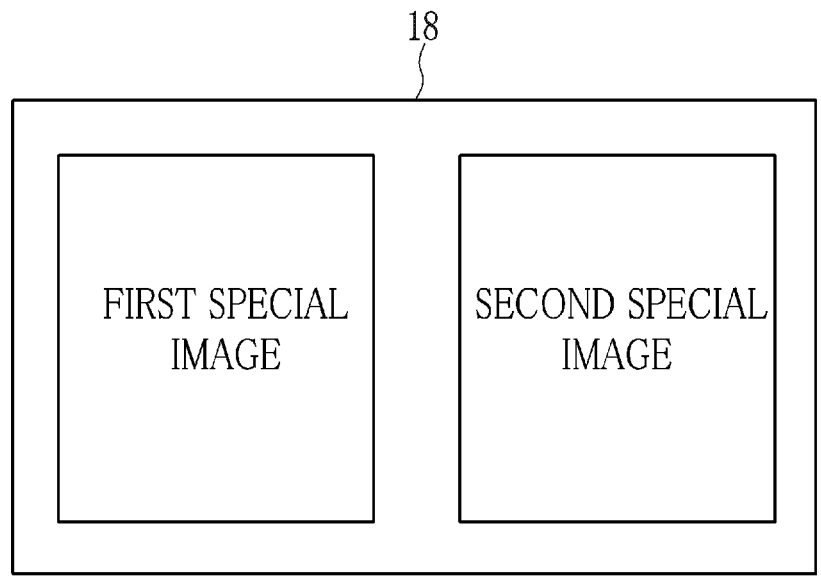
FIG. 24 is an image view of a monitor which displays a first special image and a second special image at a time.

Based on the first special image produced by the first special image processor 64a and the second special image produced by the second special image processor 64b, the simultaneous display image processor 64c produces a special image for simultaneous display. As illustrated in FIG. 24, the monitor 18 displays the first special image on one side of the monitor 18 and the second special image on the other side of the monitor 18, based on the special image for simultaneous display. In the first special image, a boundary between the normal portion and the atrophic portion is clear enough to facilitate finding the position of the atrophic portion or the like. However, the normal portion is displayed in pseudo color, which is not the actual color of the gastric mucosa (mucous membrane layer of the stomach). The pseudo color gives a doctor an unnatural impression. In the second special image, as compared with the first special image, the boundary between the normal portion and the atrophic portion is clear to some extent, but the color of the normal portion is displayed in actual color of the stomach, so that the second special image gives a doctor a natural impression. The simultaneous display of the first and second special images allows a doctor to detect the boundary of the normal portion and the atrophic portion while checking the color of the normal portion.

Figure 25:
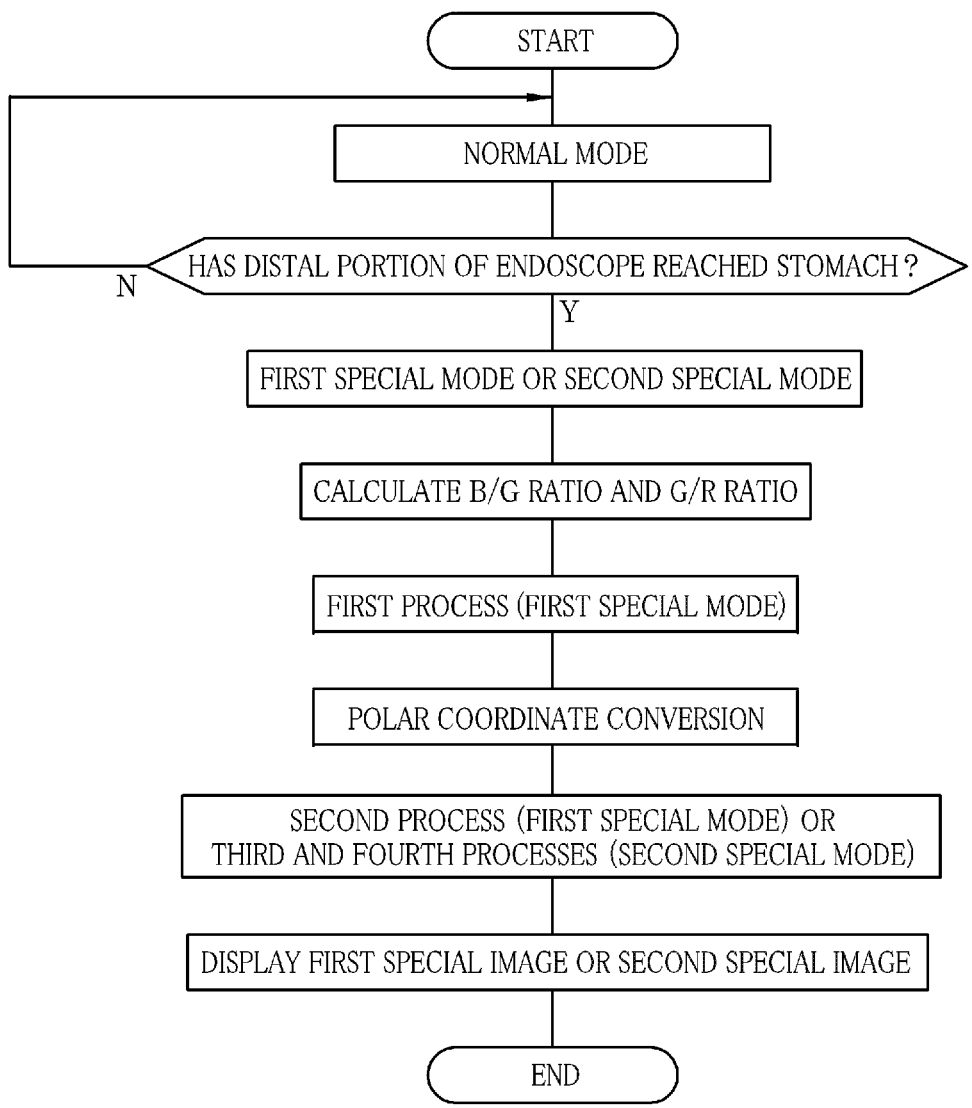
FIG. 25 is a flowchart illustrating steps of the present invention.

Hereinafter, referring to a flowchart in FIG. 25, an operation of the present invention is described. First, the mode is set to the normal mode. The insertion section 12a of the endoscope 12 is inserted into the body cavity. After the distal portion 12d of the insertion section 12a reached the stomach, the mode SW 13a is operated to switch from the normal mode to the first or second special mode. Note that the mode is switched to the simultaneous display mode in the case where a doctor performs a diagnosis of the atrophic gastritis while observing both of the first and second special images.

Based on the RGB image signals obtained after the mode is switched to the first or second special mode, the signal ratio calculator 72 calculates the B/G ratio and the G/R ratio. Then, in a case where the mode is set to the first special mode, the first process (for the signal ratio space) is performed. The signal ratio space is formed by the B/G ratio and the G/R ratio. In the first process, the coordinates corresponding to the first observation area, the coordinates corresponding to the second observation area, and the coordinates corresponding to the third observation area are moved in a parallel manner such that the coordinates corresponding to the second observation area are moved to the reference area. In the first observation area, the normal mucosa is distributed. In the second observation area, atrophic mucosa damaged (or shrunk) due to the atrophic gastritis is distributed. In the third observation area, the deep blood vessels, which are located beneath the atrophic mucosa and seen through the atrophic mucosa, are distributed.

Next, in either of the first and second special modes, the B/G ratio and the G/R ratio are converted into a radial coordinate r and an angle θ by the polar coordinate conversion. In the first special mode, the second process for the signal ratio space is performed based on the radial coordinate r and an angle θ obtained after the first process for the signal ratio space and the polar coordinate conversion. In the second process, the coordinates corresponding to the first observation area and the coordinates corresponding to the third observation area are moved away from each other. The radial coordinate r and an angle θ obtained after the second process are converted into Cartesian coordinates through Cartesian coordinate conversion. The first special image is produced based on the B/G ratio and the G/R ratio obtained after the Cartesian coordinate conversion. The first special image is displayed on the monitor 18.

In the second special mode, the third process (for the signal ratio space) is performed. In the third process, the coordinates corresponding to the second observation area are moved to the reference area while the coordinates corresponding to the first and third observation areas are maintained unchanged, based on the radial coordinate r and the angle θ obtained after the polar coordinate conversion. Then the fourth process (for the signal ratio space) is performed. In the fourth process, the coordinates corresponding to the third observation area are moved while the coordinates corresponding to the first observation area are maintained unchanged, based on the radial coordinate r and the angle θ obtained after the third process. The radial coordinate r and the angle θ obtained after the fourth process are converted into Cartesian coordinates through the Cartesian coordinate conversion. A second special image is produced based on the B/G and G/R ratios obtained after the Cartesian coordinate conversion. The second special image is displayed on the monitor 18.

Note that, in the simultaneous display mode, the simultaneous display is not limited to that of the first special image and the second special image. For example, the first special image and the normal image may be displayed simultaneously, or the second special image and the normal image may be displayed simultaneously. In those cases, the normal image and the special image are produced in the normal image processor 62 and the special image processor 64, respectively, and displayed on the monitor 18 through the video signal generator 66.

In the simultaneous display mode, the first special image and a third special image may be displayed simultaneously. The third special image refers to an image which has not been subjected to any of the first to third processes. The third special image is produced by a third special image processor (not shown) provided in the special image processor 64. Unlike the first special image processor 64a, the third special image processor is not provided with the parallel movement section 73, the polar coordinate converter 74, the angle expansion/compression unit 75, the Cartesian coordinate converter 76, and the RGB converter 77. Other than those, the third special image processor is similar to the first special image processor 64a. Note that in the case of producing the third special image, it is preferred that the light of each color is emitted with the light intensity of the violet light V greater than those of the blue light B, the green light G, and the red light R. In the third special image taken under the light of such emission conditions, the surface blood vessels are enhanced while the excellent brightness of the entire image is maintained.

Note that, in the above embodiment, the signal ratio calculator 72 calculates the B/G ratio and the G/R ratio based on the first RGB image signals. The first to fourth processes are performed in the feature space formed by the B/G ratio and the G/R ratio. Alternatively, two or more pieces of color information which differ from the B/G ratio and the G/R ratio may be obtained. The first to fourth processes may be performed in a feature space formed by the two or more pieces of color information.

Figure 26:
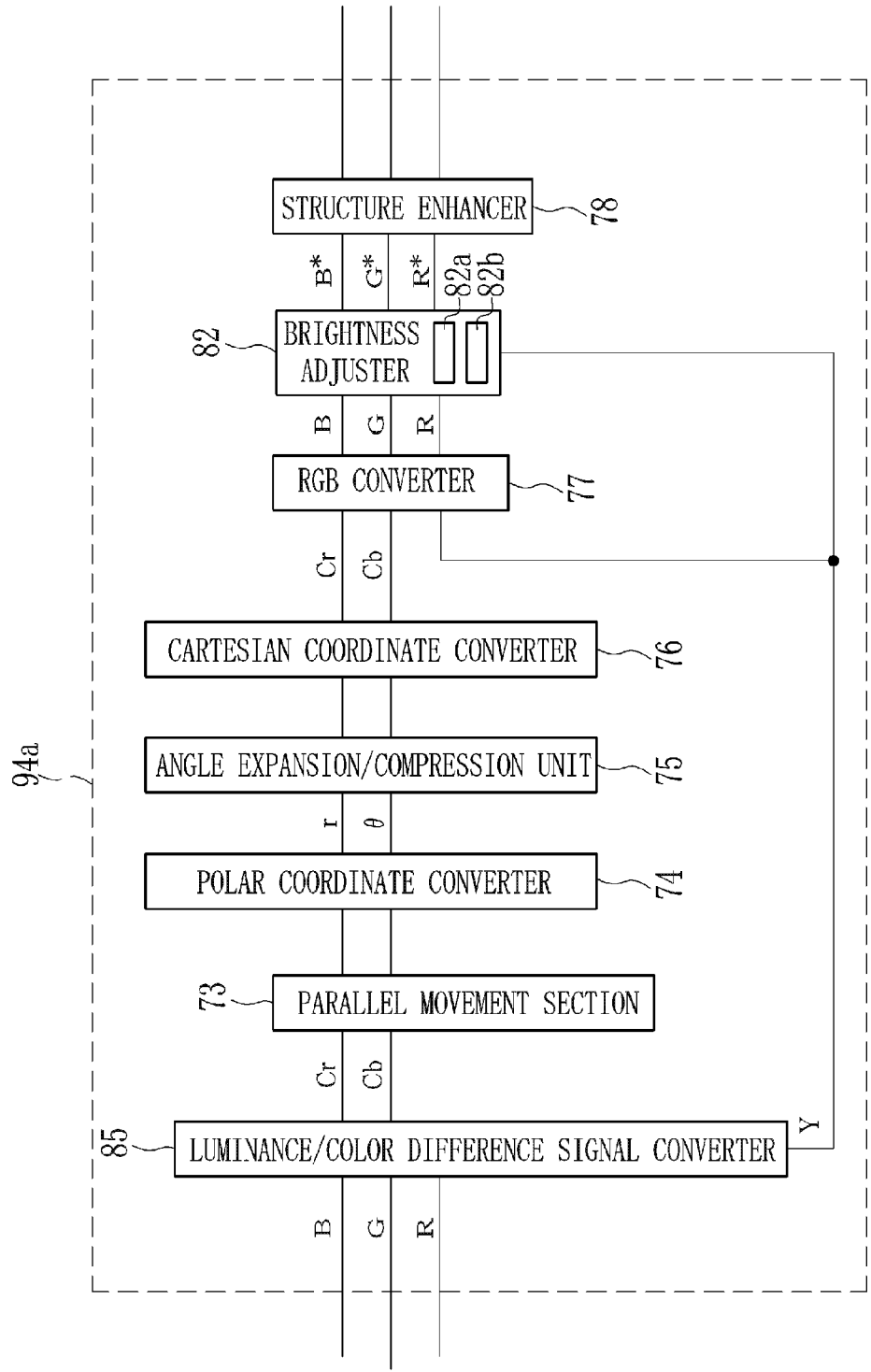
FIG. 26 is a block diagram illustrating functions of a first special image processor used for Cb-Cr space formed by Cr and Cb.

For example, color difference signals Cr and Cb may be obtained as the color information. The first to fourth processes may be performed in a feature space formed by the color difference signals Cr and Cb. In the case where the first special image is produced by using the color difference signals Cr and Cb, a first special image processor 94a illustrated in FIG. 26 is used. Unlike the first special image processor 64a, the first special image processor 94a is not provided with the inverse gamma converter 70, the log converter 71, the signal ratio calculator 72, the inverse log converter 79, and the gamma converter 80. Instead, the first special image processor 94a comprises a luminance/color difference signal converter 85. The components, other than those described above, of the first special image processor 94a are the same as or similar to the components of the first special image processor 64a.

The luminance/color difference signal converter 85, which corresponds to the "color information obtaining section" of the present invention, converts the first RGB image signals into the luminance signal Y and the color difference signals Cr and Cb. A well-known conversion equation is used for the conversion into the color difference signals Cr and Cb. The color difference signals Cr and Cb are transmitted to the parallel movement section 73. The luminance signal Y is transmitted to the RGB converter 77 and the brightness adjuster 82. The RGB converter 77 converts the color difference signals Cr and Cb, which have passed through the Cartesian coordinate converter 76, and the luminance signal Y into the second RGB image signals. The brightness adjuster 82 adjusts the pixel values of the second RGB image signals with the use of the luminance signal Y (the first brightness information Yin) and the second brightness information (the second brightness information Yout) which is calculated by the second brightness information calculator 82b. Note that the method for calculating the second brightness information Yout and the method for adjusting the pixel values of the second RGB image signals are the same as or similar to those of the first special image processor 64a.

Figure 27:
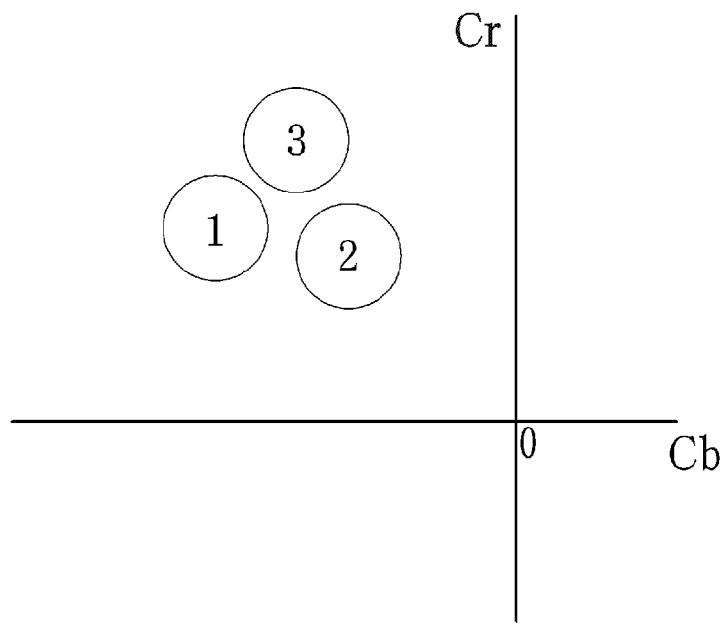
FIG. 27 is an explanatory view illustrating a positional relationship among the first, second, and third observation areas in the Cb-Cr space.

The first special image processor 94a performs the first process and the second process (for the Cb-Cr space) in the feature space (hereinafter referred to as the Cb-Cr space; the vertical axis: the color difference signal Cr, the horizontal axis: the color difference signal Cb) to produce the first special image. In the Cb-Cr space, as illustrated in FIG. 27, the second observation area (denoted as "2") is closest to the origin point. The first and third observation areas (denoted as "1" and "3", respectively) are located farther from the origin point than is the second observation area. The first observation area is located close to the horizontal axis Cb. The third observation area is located close to the vertical axis Cr.

Figure 28:
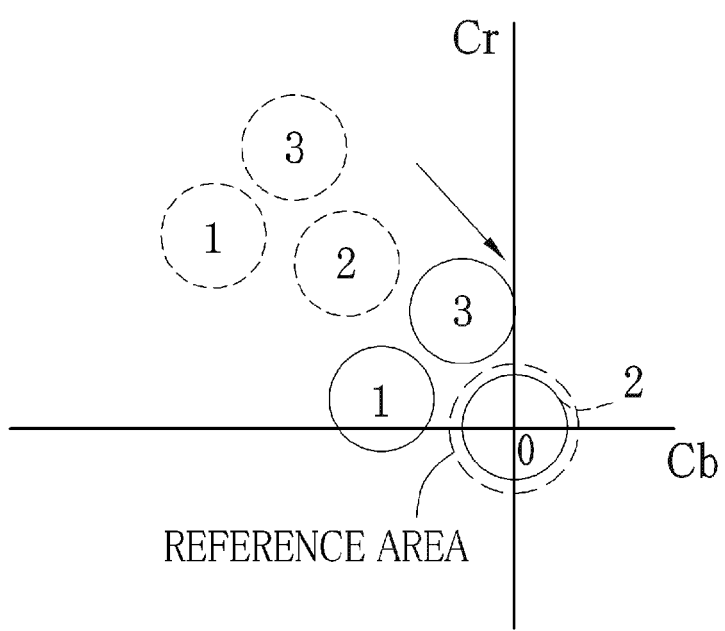
FIG. 28 is an explanatory view illustrating a first process in the Cb-Cr space.

In the first process (for the Cb-Cr space), as illustrated in FIG. 28, the parallel movement section 73 performs processing to move all of the coordinates corresponding to the first to third observation areas in a parallel manner such that the coordinates corresponding to the second observation area are moved to the reference area containing the origin point of the Cb-Cr space. The parallel movement made by the parallel movement section 73 is the same as or similar to that of the case of the signal ratio space. The reference area refers to a region with low chroma or saturation, excluding the first and third observation areas which have been subjected to the first process (for the Cb-Cr space).

Figure 29:
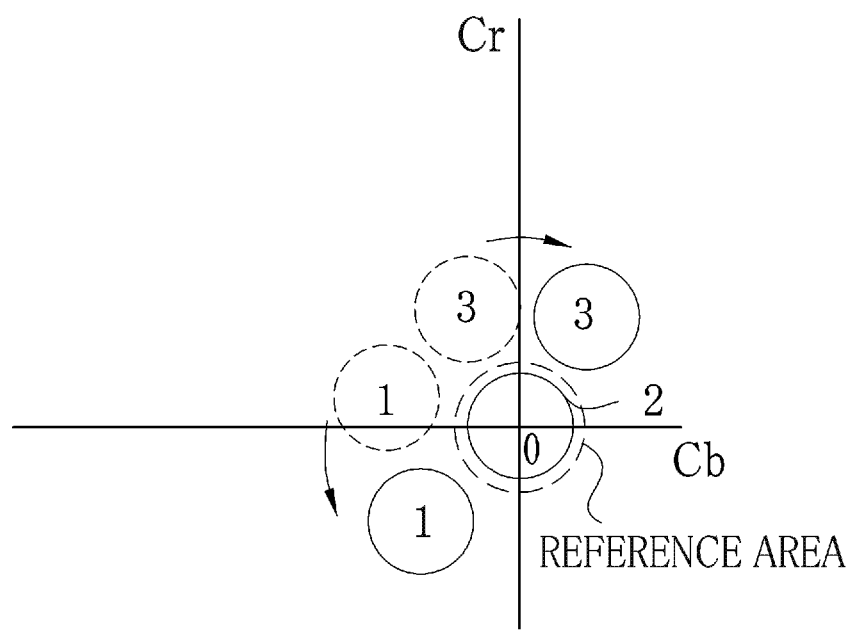
FIG. 29 is an explanatory view illustrating a second process in the Cb-Cr space.

Note that, in FIGS. 28 and 29, the areas before the first process (for the Cb-Cr space) are depicted with dotted lines. The areas after the first process are depicted with solid lines. This also applies to the drawings described below. Here, "1", "2", and "3" denote the first, second, and third observation areas, respectively (the same hereinafter).

In the second process (for the Cb-Cr space), as illustrated in FIG. 29, the angle expansion/compression unit 75 performs processing to move the coordinates which correspond to the first observation area and the coordinates which correspond to the third observation area away from each other while the coordinates which correspond to the second observation area are maintained in the reference area. The method for moving the coordinates which correspond to the first and third observation areas are similar to that in the signal ratio space. In other words, the coordinates are moved by the expansion or the compression of the angle (angular coordinate).

Figure 30:
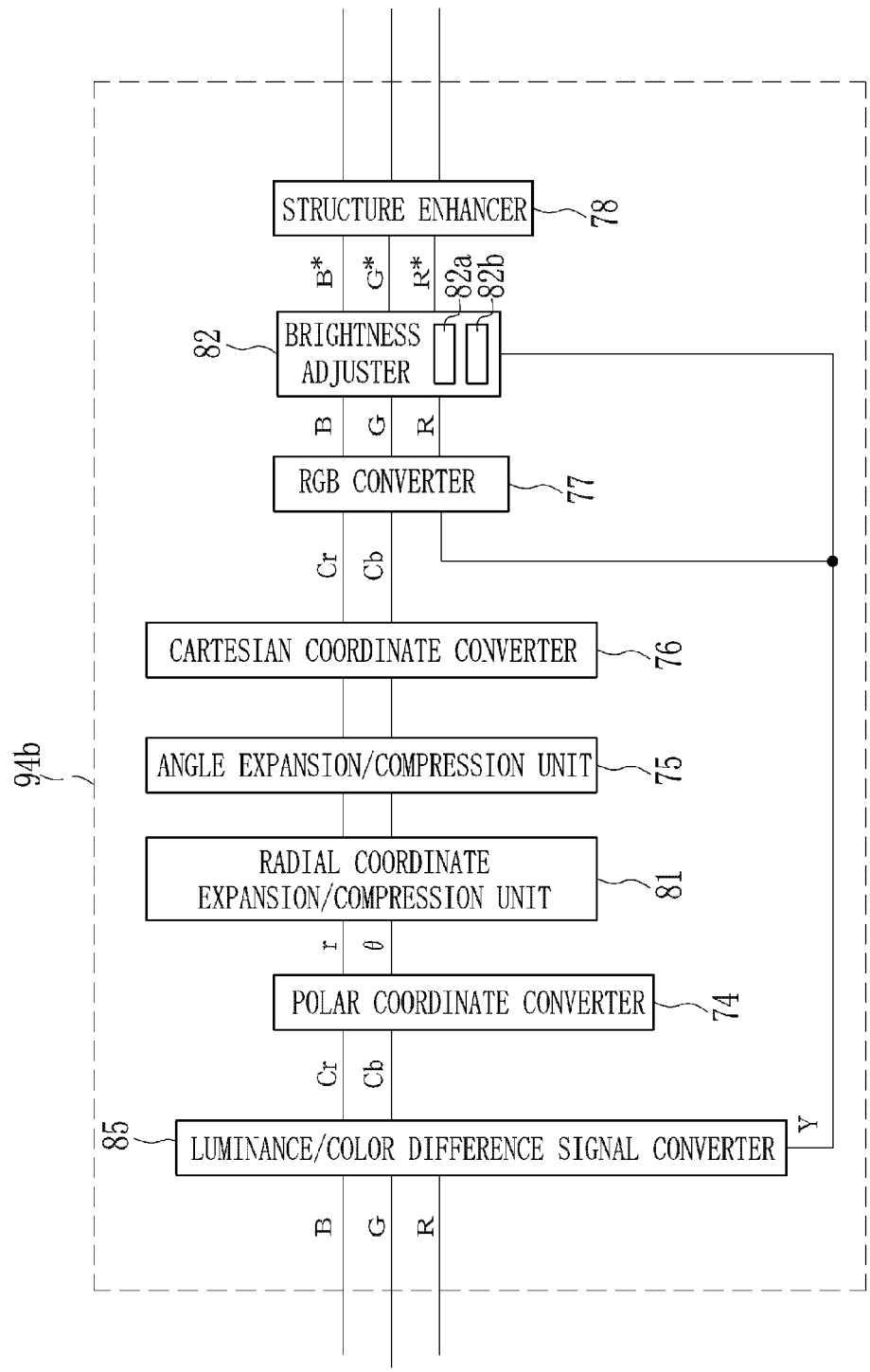
FIG. 30 is a block diagram illustrating functions of a second special image processor used for the Cb-Cr space.

In the case where the second special image is produced by using the color difference signals Cr and Cb, a second special image processor 94b (see FIG. 30) is used. Unlike the second special image processor 64b, the second special image processor 94b is not provided with the inverse gamma converter 70, the Log converter 71, the signal ratio calculator 72, the inverse Log converter 79, and the gamma converter 80. Instead, the second special image processor 94b comprises the luminance/color difference signal converter 85. Other than those, the components of the second special image processor 94b are the same as or similar to those of the second special image processor 64b. Note that the functions of the luminance/color difference signal converter 85, the RGB converter 77, and the brightness adjuster 82 are the same as or similar to those of the first special image processor 94a, so that the descriptions thereof are omitted.

Figure 31:
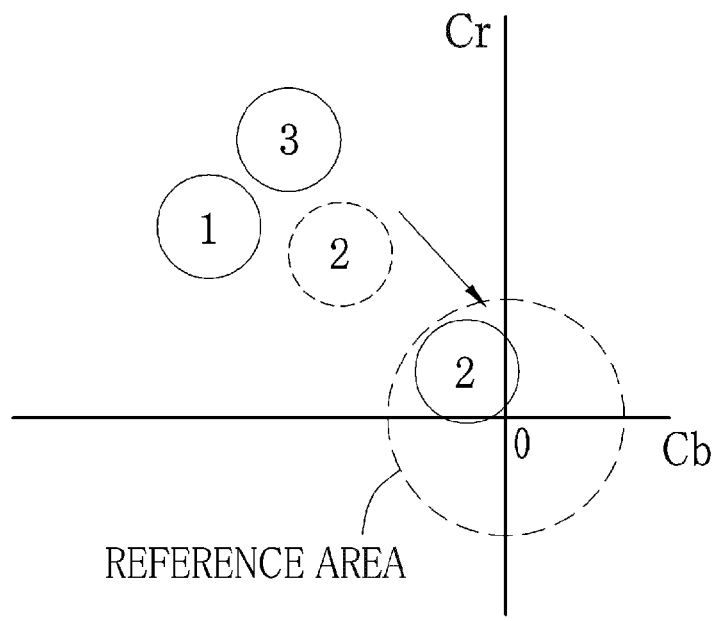
FIG. 31 is an explanatory view illustrating a third process in the Cb-Cr space.

The second special image processor 94b performs the third process and the fourth process (for the Cb-Cr space) in the Cb-Cr space to produce the second special image. In the third process (for the Cb-Cr space), as illustrated in FIG. 31, the radial coordinate expansion/compression unit 81 performs processing to move the coordinates which correspond to the second observation area to the reference area that contains the origin point of the Cb-Cr space while the coordinates which correspond to the first observation area and the coordinates which correspond to the third observation area are maintained unchanged. The method for moving the coordinates which correspond to the second observation area is the same as or similar to that in the signal ratio space. In other words, the coordinates which correspond to the second observation area are moved by expanding or compressing the radial coordinates.

Figure 32:
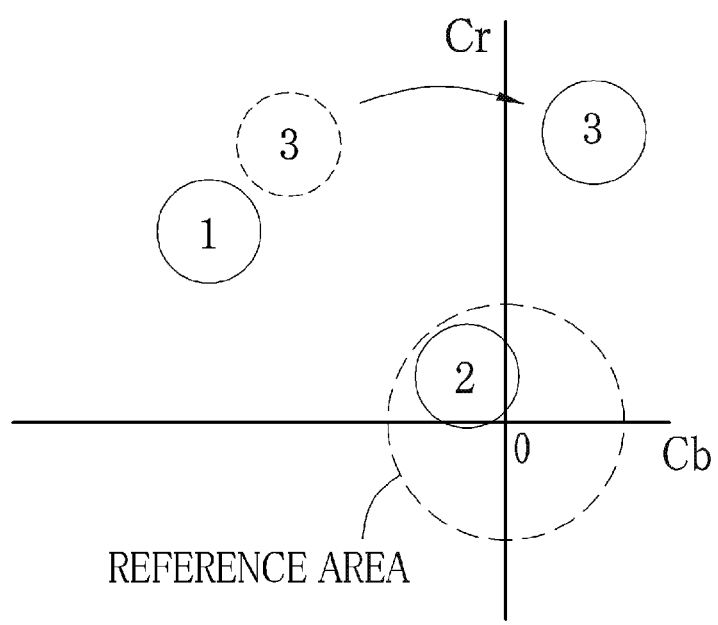
FIG. 32 is an explanatory view illustrating a fourth process in the Cb-Cr space.

As illustrated in FIG. 32, in the fourth process (for the Cb-Cr space), the angle expansion/compression unit 75 performs processing to move only the coordinates which correspond to the third observation area away from the coordinates which correspond to the first observation area while the coordinates which correspond to the second observation area are maintained within the reference area and while the coordinates which correspond to the first observation area are maintained unchanged. The method for moving the coordinates which correspond to the third observation area is the same as or similar to that in the case of the signal ratio space, and performed by expanding or compressing the angle (angular coordinate).

Figure 33:
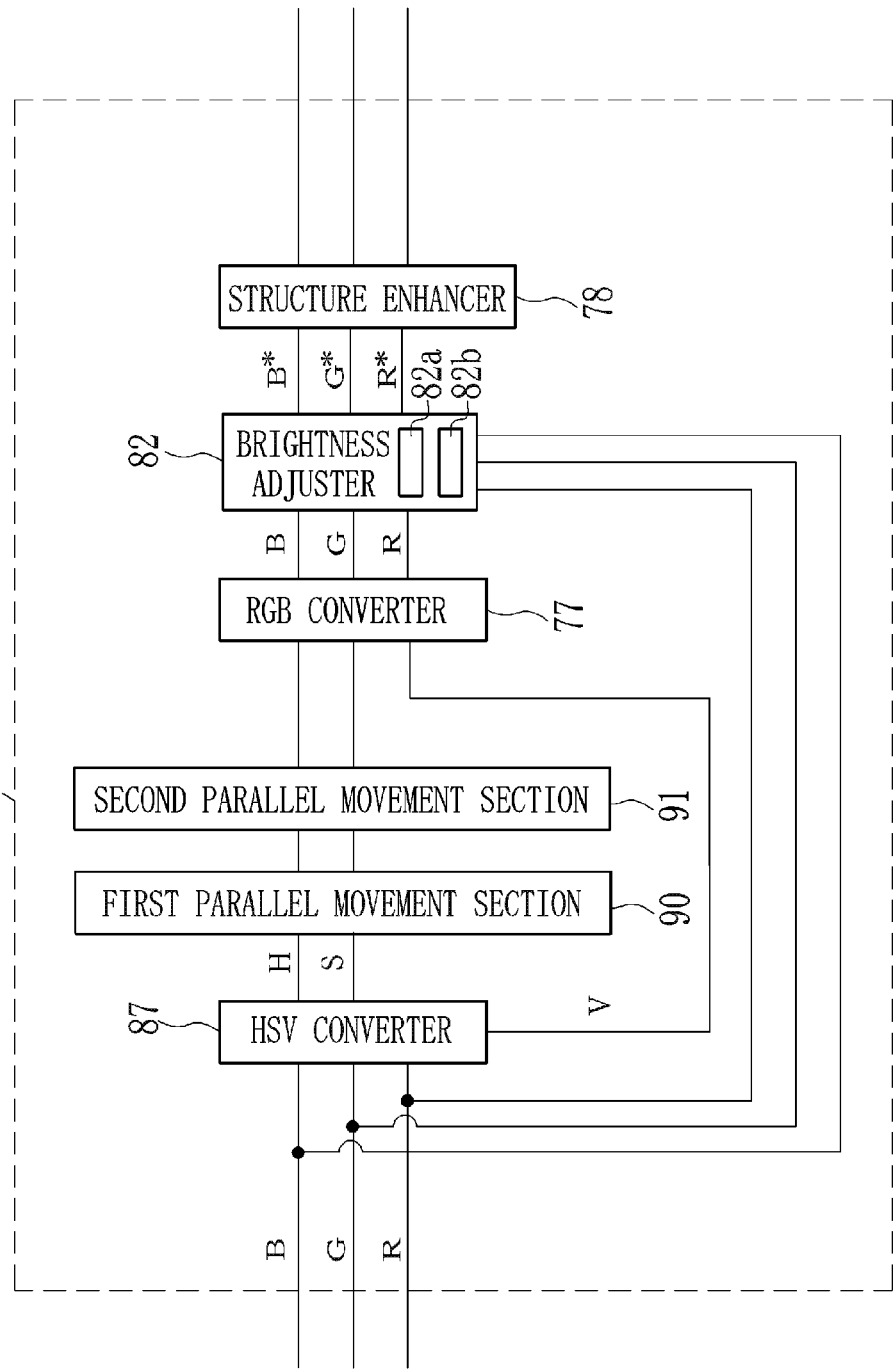
FIG. 33 is a block diagram illustrating functions of the first special image processor in HS space formed by H(hue) and S(saturation)

The color information may be hue H and saturation S. The first to fourth processes may be performed in the feature space (HS space) formed by the hue H and the saturation S. In the case where the first special image is produced by using the hue H and the saturation S, a first special image processor 96a (see FIG. 33) is used. Unlike the first special image processor 64a, the first special image processor 96a is not provided with the inverse gamma converter 70, the Log converter 71, the signal ratio calculator 72, the parallel movement section 73, the polar coordinate converter 74, the angle expansion/compression unit 75, the Cartesian coordinate converter 76, the inverse Log converter 79, and the gamma converter 80. Instead, the first special image processor 96a comprises an HSV converter 87, a first parallel movement section 90, and a second parallel movement section 91. The first and second parallel movement sections 90 and 91 are placed between the HSV converter 87 and the RGB converter 77. Other than those, the first special image processor 96a is the same as or similar to the first special image processor 64a.

The HSV converter 87, which corresponds to the "color information obtaining section" of the present invention, converts the first RGB image signals into hue H, saturation S, and value (lightness or brightness) V. Well-known conversion equations are used for the conversion into the hue H, the saturation S, and the value V. The hue H and the saturation S are transmitted to the first parallel movement section 90. The value V is transmitted to the RGB converter 77. The RGB converter 77 converts the hue H and the saturation S, which have passed through the second parallel movement section 91, and the value V, which is transmitted from the HSV converter 87, into the second RGB image signals. The brightness adjuster 82 adjusts the pixel values of the second RGB image signals with the use of the first brightness information Yin calculated by the first brightness information calculator 82a and the second brightness information Yout calculated by the second brightness information calculator 82b. Note that the methods for calculating the first brightness information Yin and the second brightness information Yout and the method for adjusting the pixel values of the second RGB image signals are the same as or similar to those of the first special image processor 64a.

Figure 34:
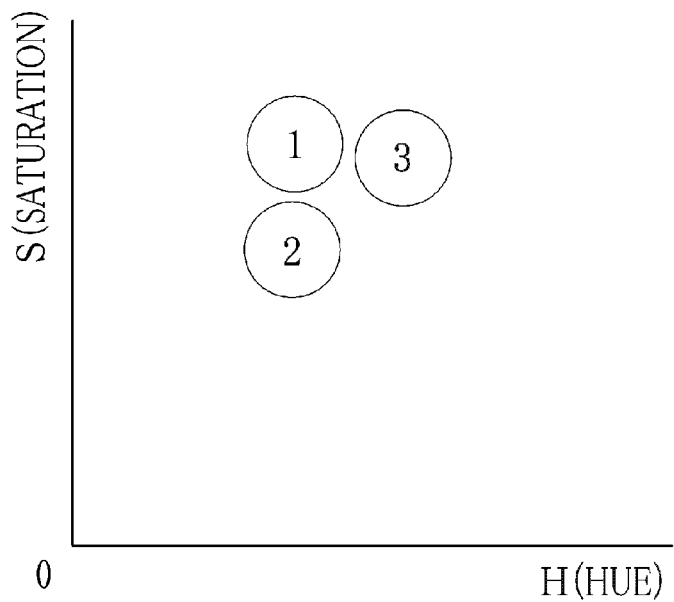
FIG. 34 is an explanatory view illustrating a positional relationship among the first, second, and third observation areas in the HS space.
Figure 35:
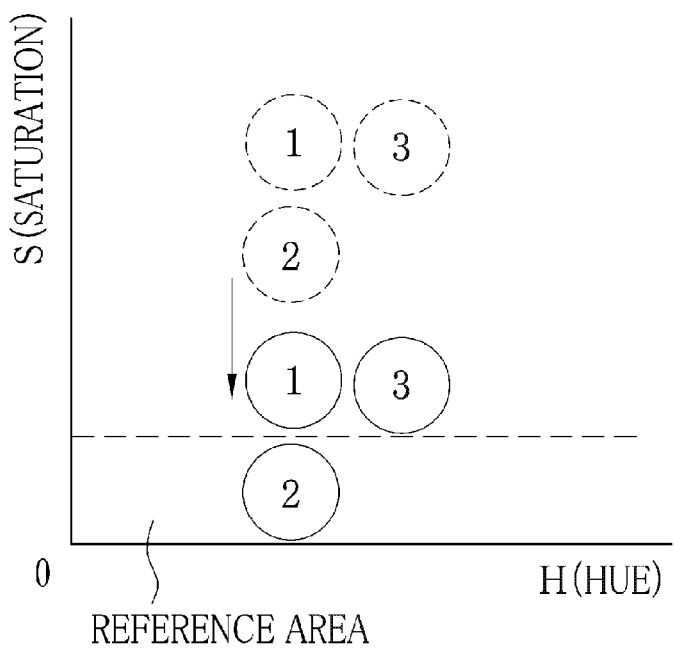
FIG. 35 is an explanatory view illustrating a first process in the HS space.

The first special image processor 96a performs the first and second processes (for HS space) to produce the first special image. As illustrated in FIG. 34, in the HS space, the second observation area is located lower than the first observation area in the saturation direction (the vertical axis). The third observation area is located to the right of the first and second observation areas in the hue direction (the horizontal axis). In the HS space, as illustrated in FIG. 35, in the first process (for the HS space), the first parallel movement section 90 moves all of the coordinates which correspond to the first observation area, all of the coordinates which correspond to the second observation area, and all of the coordinates which correspond to the third observation area in a parallel manner so as to move the coordinates which correspond to the second observation area to the reference area. Here, the reference area in the HS space is a region with low saturation and contains the origin point of the HS space, but excludes the coordinates which correspond to the first and third observation areas obtained after the first process (for the HS space). The first parallel movement section 90 translates or moves the coordinates which correspond to the first observation area, the coordinates which correspond to the second observation area, and the coordinates which correspond to the third observation area downward in a parallel manner. The information related to the hue H and the saturation S obtained after the parallel movement is transmitted to the second parallel movement section 91.

Figure 36:
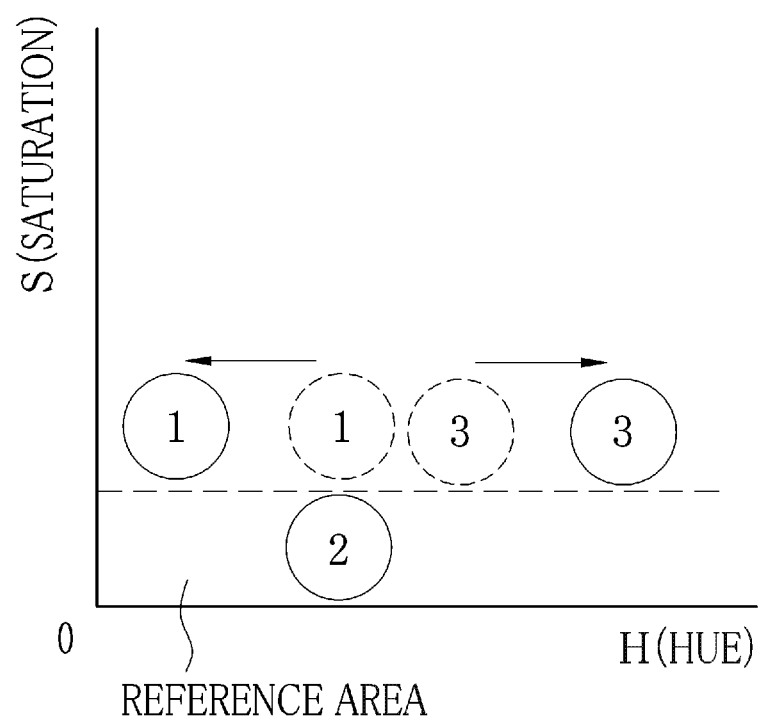
FIG. 36 is an explanatory view illustrating a second process in the HS space.

As illustrated in FIG. 36, in the second process (for the HS space) after the parallel movement by the first parallel movement section 90, the coordinates which correspond to the first observation area and the coordinates which correspond to the third observation area are moved away from each other in a parallel manner while the coordinates which correspond to the second observation area are maintained in the reference area. The second parallel movement section 91 moves the coordinates which correspond to the first observation area to the left in the hue direction in a parallel manner, and moves the coordinates which correspond to the third observation area to the right in the hue direction in a parallel manner.

Figure 37:
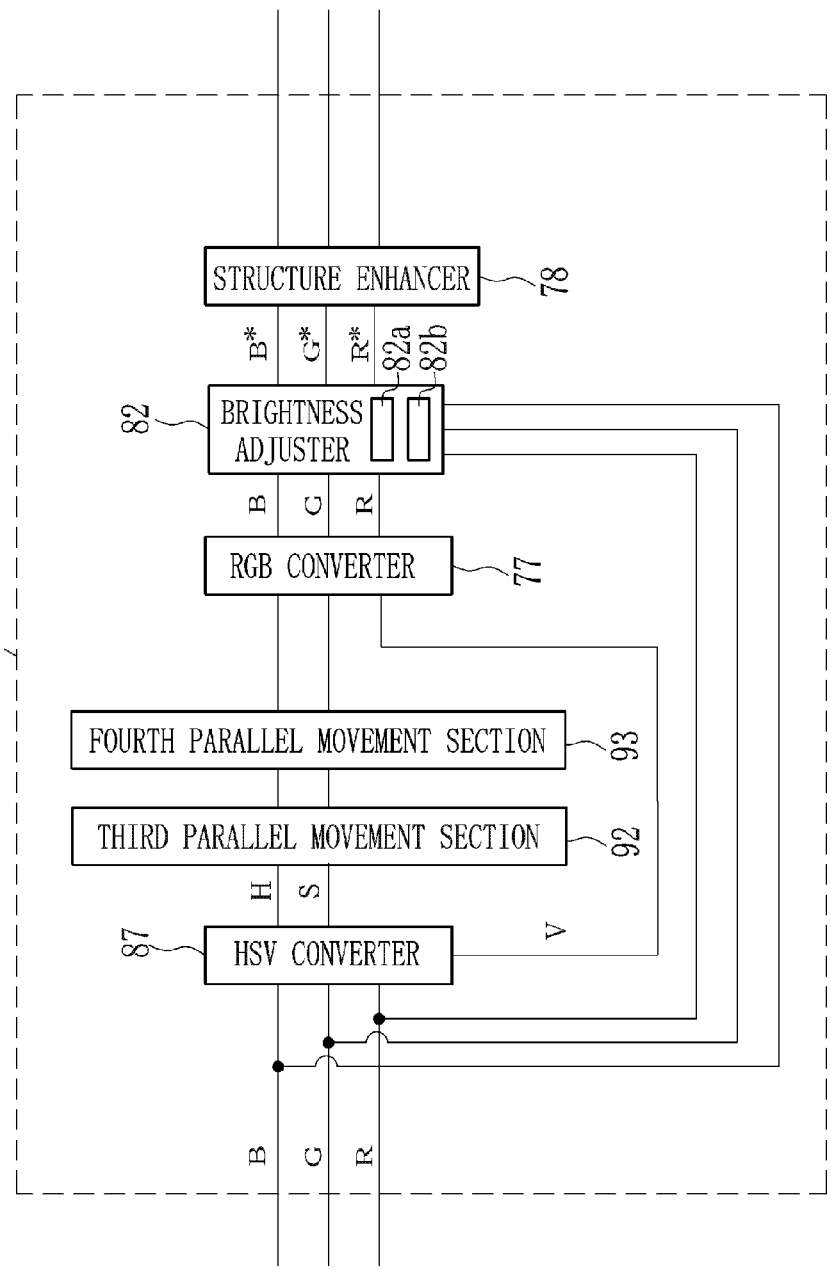
FIG. 37 is a block diagram illustrating functions of the second special image processor used for the HS space.

In the case where the second special image is produced by using the hue H and the saturation H, a second special image processor 96b (see FIG. 37) is used. The second special image processor 96b is similar to the first special image processor 96a, but differs from the first special image processor 96a in that the second special image processor 96b is provided with a third parallel movement section 92, in place of the first parallel movement section 90, and a fourth parallel movement section 93 in place of the second parallel movement section 91. Note that the functions of the HSV converter 87, the RGB converter 77, and the brightness adjuster 82 of the second special image processor 96b are the same as or similar to those of the first special image processor 96a, so that the descriptions thereof are omitted.

Figure 38:
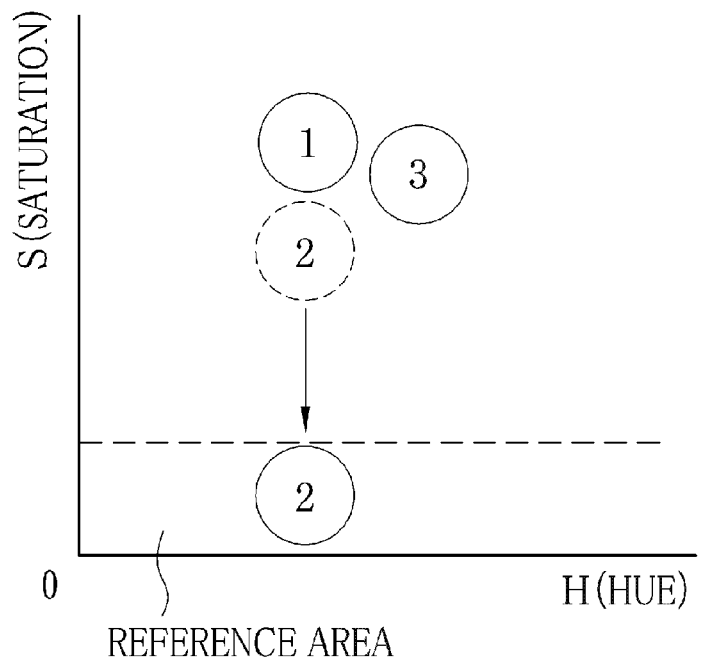
FIG. 38 is an explanatory view illustrating a third process for the HS space.

The second special image processor 96b performs the third and fourth processes (for the HS space) in the HS space to produce the second special image. In the third process (for the HS space), as illustrated in FIG. 38, the third parallel movement section moves the coordinates which correspond to the second observation area downward in the saturation direction in a parallel manner while the coordinates which correspond to the first observation area and the coordinates which correspond to the third observation area are maintained unchanged. Here, the reference area in the HS space is a region with low saturation which contains the origin point of the HS space, but excludes the coordinates which correspond to the first and third observation areas obtained after the first process (for the HS space). The information related to the hue (H) and the saturation (S) obtained after the parallel movement are transmitted to the fourth parallel movement section 93.

Figure 39:
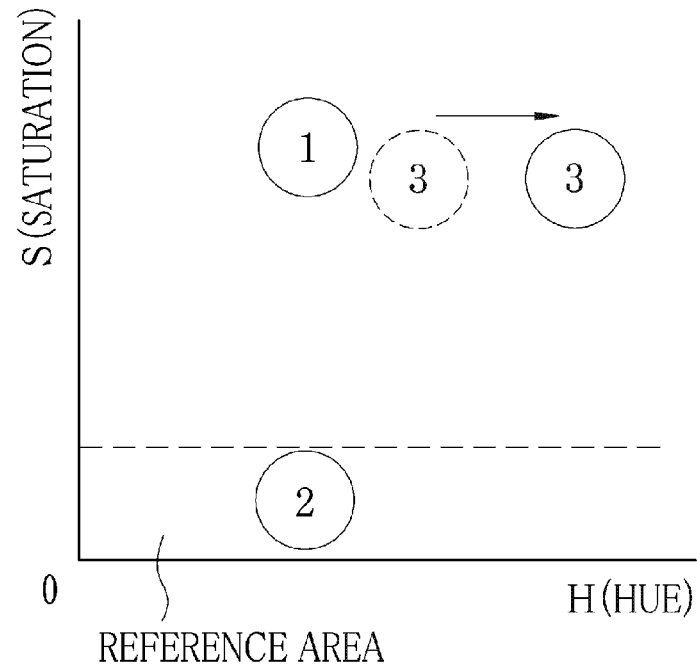
FIG. 39 is an explanatory view illustrating a fourth process for the HS space.

In the fourth process (for the HS space), as illustrated in FIG. 39, the coordinates which correspond to the third observation area are moved to the right in the hue direction in a parallel manner while the coordinates which correspond to the second observation area are maintained in the reference area and while the coordinates which correspond to the first observation area are maintained unchanged.

Second Embodiment

In the second embodiment, a laser and a phosphor are used, instead of the LEDs 20a to 20d of the four colors described in the first embodiment, to illuminate the object. Other than that, the configuration is the same as or similar to that in the first embodiment.

Figure 40:
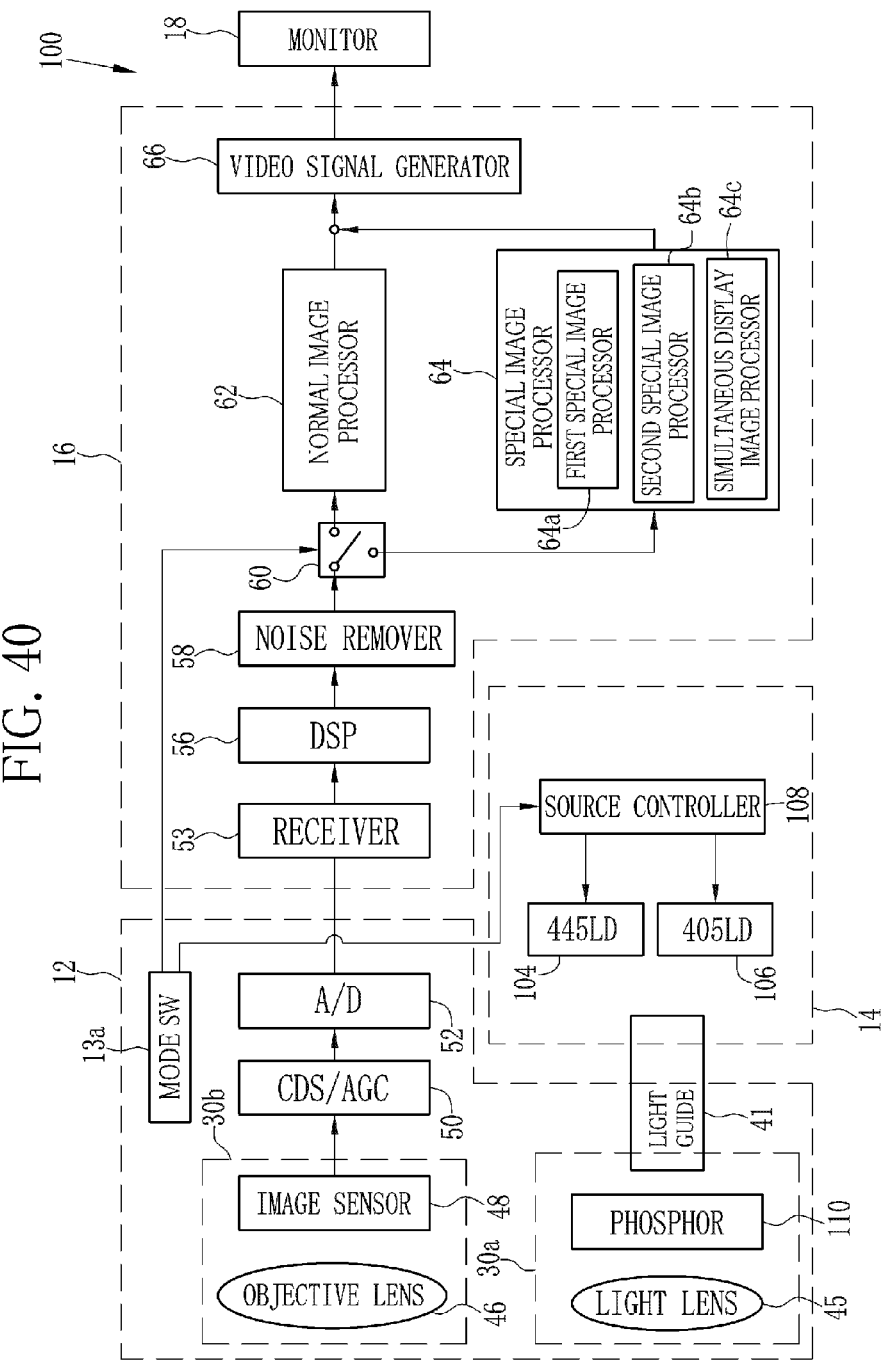
FIG. 40 is a block diagram illustrating functions of an endoscope system according to the second embodiment.

As illustrated in FIG. 40, in the light source device 14 of an endoscope system 100 according to the second embodiment, a blue laser (denoted as 445LD in FIG. 40) 104 and a blue-violet laser (denoted as 405LD in FIG. 40) 106 are provided in place of the LEDs 20a to 20d of the four colors. The blue laser 104 emits blue laser beams with the center wavelength 445±10 nm. The blue-violet laser 106 emits blue-violet laser beams with the center wavelength 405±10 nm. The light emissions from the semiconductor light emitting elements of the lasers 104 and 106 are controlled individually by a source controller 108. The light quantity ratio between the light (laser beams) from the blue laser 104 and the light (laser beams) from the blue-violet laser 106 is changed as desired.

In the normal mode, the source controller 108 actuates the blue laser 104. In the first special mode, the second special mode, or the simultaneous display mode, the source controller 108 actuates and controls both the blue laser 104 and the blue-violet laser 106 such that the light-emission intensity of the blue laser beams is greater than that of the blue-violet laser beams. The laser beams emitted from each of the lasers 104 and 106 are incident on the light guide (LG) 41 through optical members (e.g. a condenser lens, an optical fiber, a combiner, and the like, all not shown).

Note that the full width at half maximum of the blue laser beams or the blue-violet laser beams is preferred to be in the order of ±10 nm. Broad-area type InGaN-based laser diodes may be used as the blue laser 104 and blue-violet laser 106. The InGaNAs-based laser diodes and the GaNAs-based laser diodes may be used instead. A light emitting element such as a light emitting diode may be used as the light source.

The illumination optical system 30a is provided with the light lens 45 and a phosphor 110 on which the blue laser beams or the blue-violet laser beams from the light guide 41 are incident. The phosphor 110 irradiated with the blue laser beams emits fluorescence. A part of the blue laser beams passes through the phosphor 110. The blue-violet laser beams pass through the phosphor 110 without exciting the phosphor. The light from the phosphor 110 is applied to the object through the light lens 45.

Figure 41:
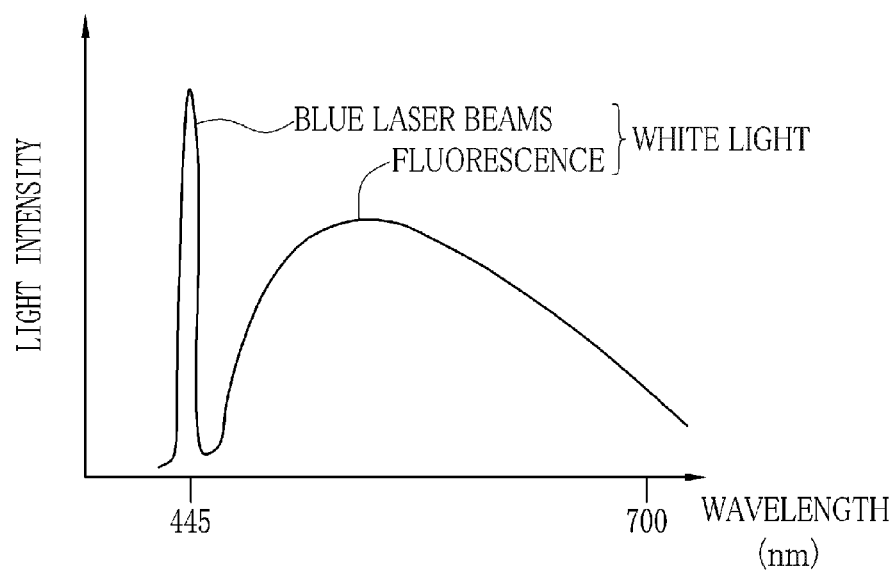
FIG. 41 is a graph illustrating an emission spectrum white light.
Figure 42:
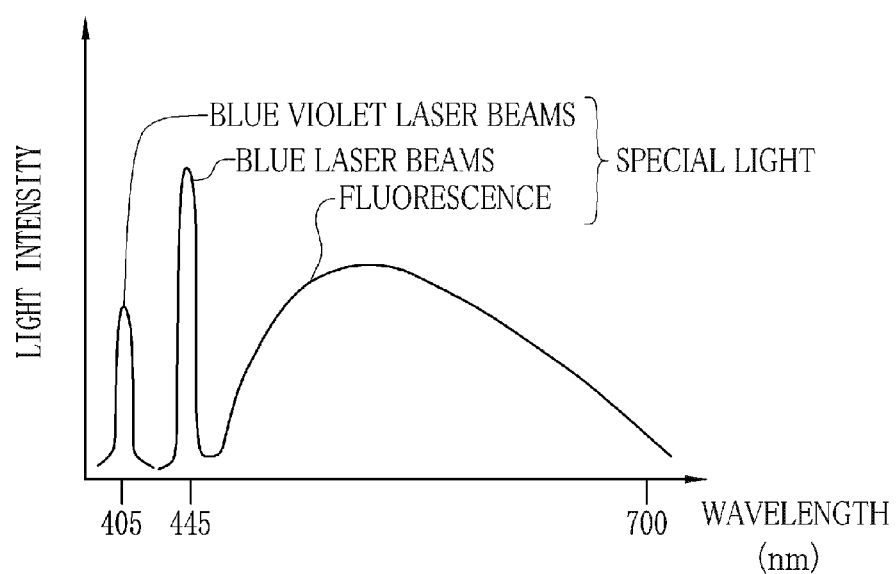
FIG. 42 is a graph illustrating an emission spectrum of special light.

Here, in the normal mode, the blue laser beams are mostly incident on the phosphor 110, so that the white light, being the combination of the blue laser beams and the fluorescence from the phosphor 110 excited by the blue laser beams, is applied to the object as illustrated in FIG. 41. In the first special mode, the second special mode, or the simultaneous display mode, both the blue-violet laser beams and the blue laser beams are incident on the phosphor 110, so that the special light, being the combination of the blue-violet laser beams, the blue laser beams, and the fluorescence from the phosphor 110 excited by the blue laser beams, is applied to the object as illustrated in FIG. 42.

Note that it is preferred to use the phosphor 110 containing two or more types of phosphor components (e.g. YAG-based phosphor, $BAM(BaMgAl_{10}O_{17})$, or the like) which absorb a part of the blue laser beams and emit light of green to yellow colors. In the case where the semiconductor light emitting elements are used as the excitation light sources for the phosphor 110 as described in this example, the high-intensity white light is provided with high light-emission efficiency, the intensity of the white light is controlled easily, and the variations in the color temperature and chromaticity of the white light are small.

Third Embodiment

In the third embodiment, instead of the LEDs 20a to 20d of the four colors described in the first embodiment, a broadband light source (e.g. a xenon lamp) and a rotary filter are used to illuminate the object. Instead of the color image sensor 48, a monochrome image sensor is used to image the object. The components other than those are the same as or similar to the components described in the first embodiment.

Figure 43:
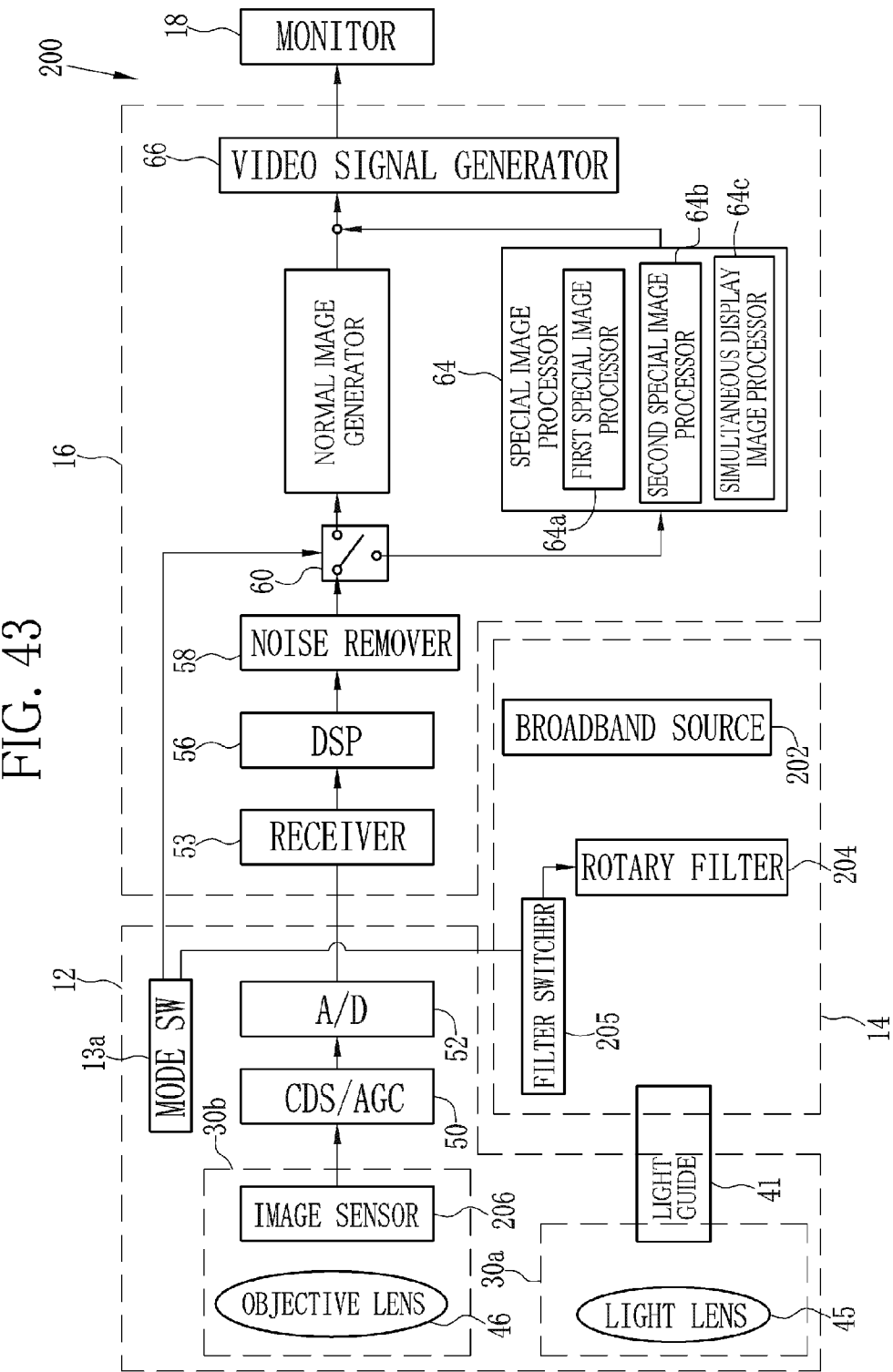
FIG. 43 is a block diagram illustrating functions of an endoscope system according to a third embodiment.

As illustrated in FIG. 43, in an endoscope system 200 of the third embodiment, a broadband light source 202, a rotary filter 204, and a filter switcher 205 are provided instead of the LEDs 20a to 20d in the light source device 14. The imaging optical system 30b is provided with a monochrome image sensor 206 with no color filter, in place of the color image sensor 48.

The broadband light source 202 is composed of a xenon lamp, a white LED, or the like, and emits the white light having the wavelength range from blue to red. The rotary filter 204 comprises a normal filter 208 provided on the inner side and a special filter 209 provided on the outer side (see FIG. 44). The filter switcher 205 shifts the rotary filter 204 in the radial direction. When the mode is set to the normal mode by the operation of the mode SW 13a, the normal filter 208 of the rotary filter 204 is inserted into the light path of the white light. When the mode is set to the first special mode, the second special mode, or the simultaneous display mode, the special filter 209 of the rotary filter 204 is inserted into the light path of the white light.

Figure 44:
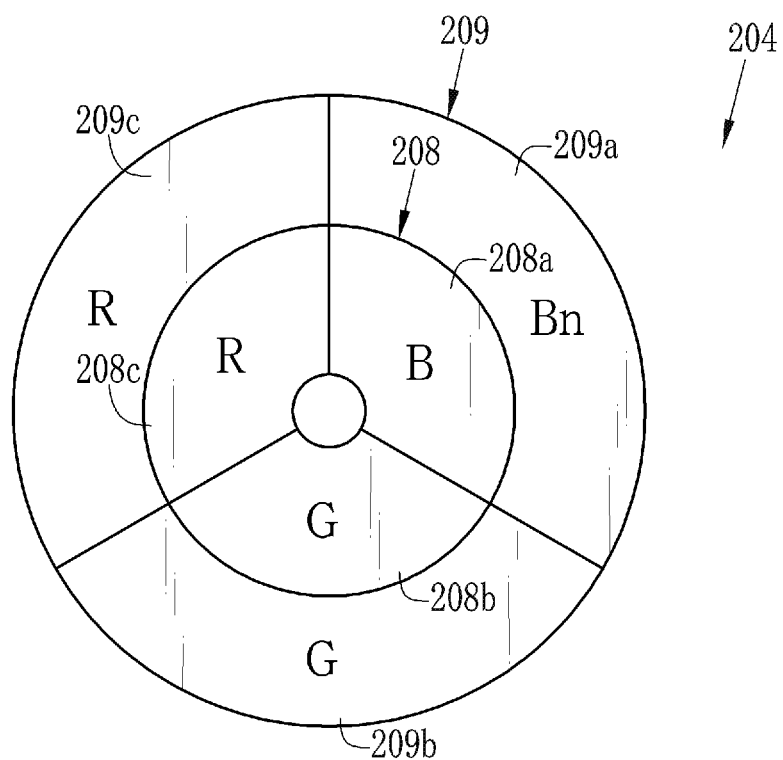
FIG. 44 is a plan view illustrating a rotary filter.

As illustrated in FIG. 44, the normal filter 208 comprises a B filter 208a, a G filter 208b, and an R filter 208c in the circumferential direction. The B filter 208a transmits the blue light of the white light. The G filter 208b transmits the green light of the white light. The R filter 208c transmits the red light of the white light. In the normal mode, the blue light, the green light, and the red light are applied in this order to the object as the rotary filter 204 is rotated.

The special filter 209 comprises a Bn filter 209a, a G filter 209b, and an R filter 209c in the circumferential direction. The Bn filter 209a transmits the blue narrowband light having a specific wavelength range of the white light. The G filter 209b transmits the green light of the white light. The R filter 209c transmits the red light of the white light. In the special mode, the blue narrowband light, the green light, and the red light are applied in this order to the object as the rotary filter 204 is rotated.

In the endoscope system 200, in the normal mode, the monochrome image sensor 206 takes an image of the object every time the blue light, the green light, or the red light is applied to the object. Thereby, the three colors (RGB) of image signals are obtained. The normal image is produced based on the RGB image signals in a manner the same or similar to that in the first embodiment.

In the first special mode, the second special mode, or the simultaneous display mode, the monochrome image sensor 206 takes an image of the object every time the blue narrowband light, the green light, or the red light is applied to the object. Thereby, the Bn image signal, the G image signal, and the R image signal are obtained. The first or second special image is produced based on the Bn image signal, the G image signal, and the R image signal. The Bn image signal is used in place of the B image signal to produce the first or second special image. Other than that, the first or second special image is produced in a manner the same as or similar to that of the first embodiment.

Fourth Embodiment

In a fourth embodiment, a swallow-type capsule endoscope is used, instead of the insertion-type endoscope 12 and the light source device 14, to obtain the RGB image signals necessary for producing the normal image, the first special image, or the second special image.

Figure 45:
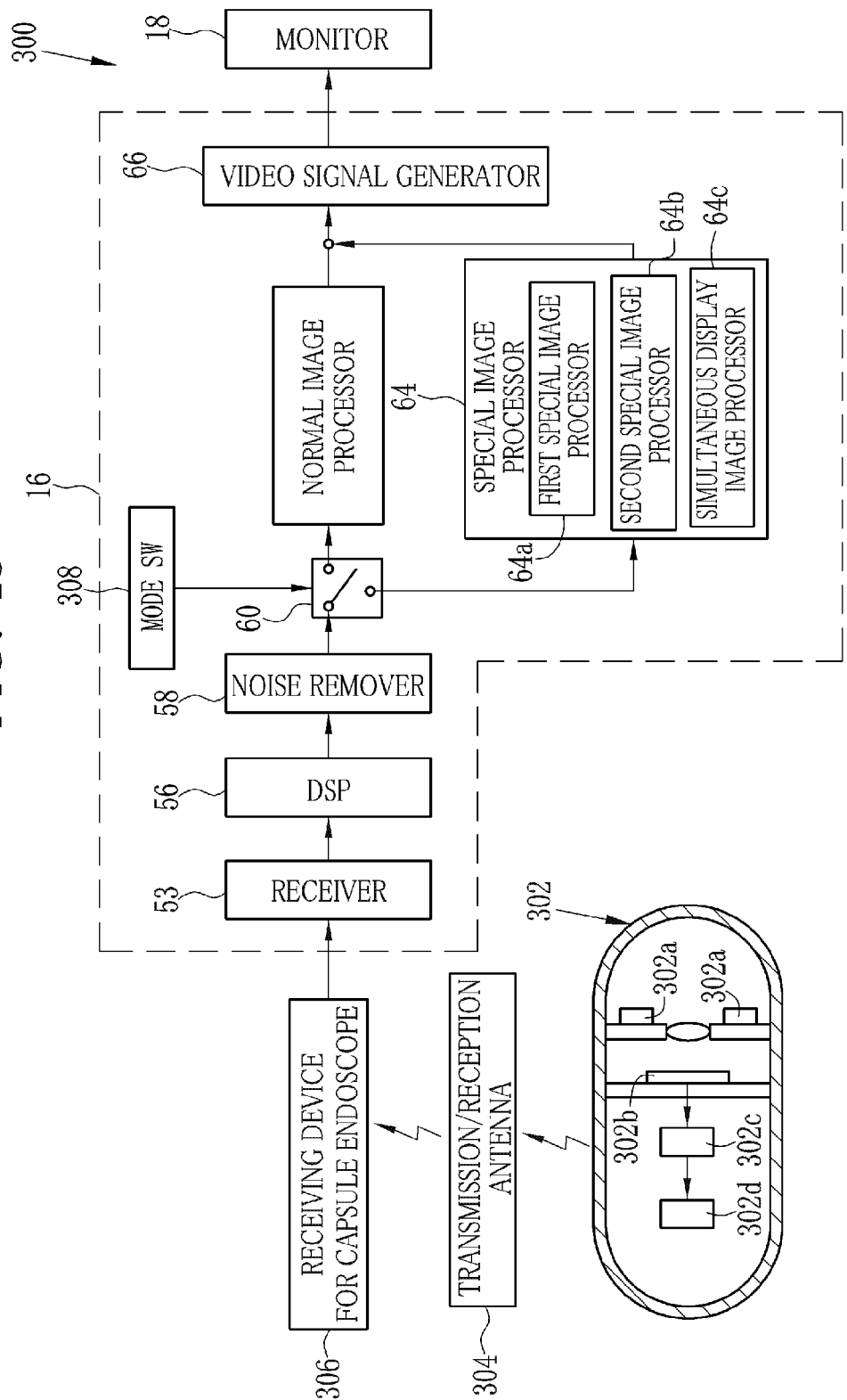
FIG. 45 is a block diagram illustrating functions of a capsule endoscope system.

As illustrated in FIG. 45, a capsule endoscope system 300 according to the fourth embodiment comprises a capsule endoscope 302, a transmission/reception antenna 304, a receiving device 306 for the capsule endoscope 302, the processor device 16, and the monitor 18. The capsule endoscope 302 comprises an LED 302a, an image sensor 302b, an image processor 302c, and a transmission antenna 302d. Note that the processor device 16 is the same as or similar to the one used in the first embodiment. In the fourth embodiment, a mode switch (SW) 308 is provided to switch among the normal mode, the first special mode, the second special mode, and the simultaneous display mode.

The LED 302a emits white light. Inside the capsule endoscope 302, two or more LEDs 302a are provided. Here, it is preferred that the LED 302a is a white light LED which comprises a blue light source and a phosphor which converts wavelengths of light from the blue light source into fluorescence. An LD (laser diode) may be used instead of the LED. The object is illuminated with the white light from the LED 302a.

The image sensor 302b is a color image sensor. The image sensor 302b takes an image of the object illuminated with the white light and outputs the RGB image signals. Here, it is preferred that the image sensor 302b is a CCD (Charge Coupled Device) image sensor or a CMOS (Complementary Metal-Oxide Semiconductor) image sensor. In the image processor 302c, the RGB image signals outputted from the image sensor 302b are subjected to a process for converting them into signals which are to be transmitted through the transmission antenna 302d. The RGB image signals, which have passed through the image processor 302c, are transmitted wirelessly from the transmission antenna 302d to the transmission/reception antenna 304.

The transmission/reception antenna 304 is affixed to the subject's body, and receives the RGB image signals from the transmission antenna 302d. The transmission/reception antenna 304 wirelessly transmits the received RGB image signals to the receiving device 306 for the capsule endoscope 302. The receiving device 306 is connected to the receiver 53 of the processor device 16, and transmits the RGB image signals, which have been received from the transmission/reception antenna 304, to the receiver 53.

Figure 46:
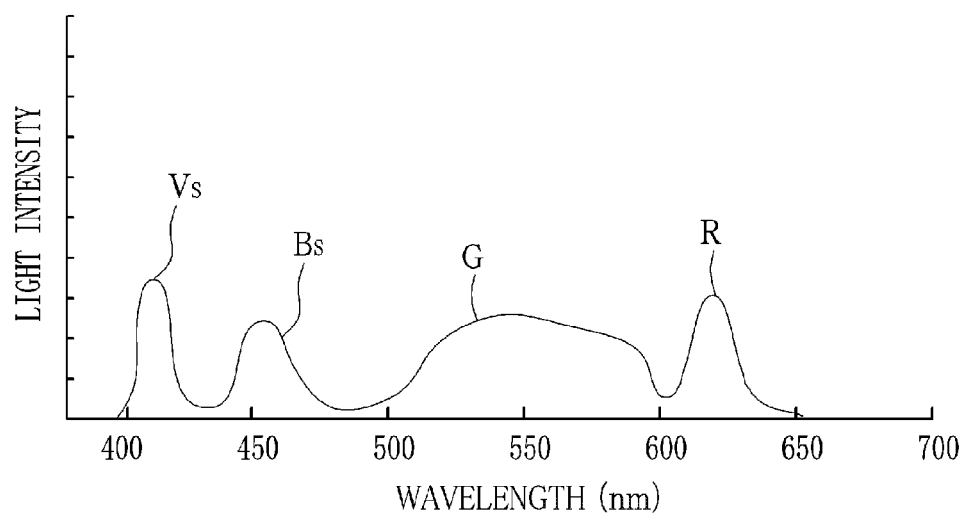
FIG. 46 is a graph illustrating emission spectrums of violet light V, blue light B, and red light R, which differ from those illustrated in FIG. 3.
Figure 47:
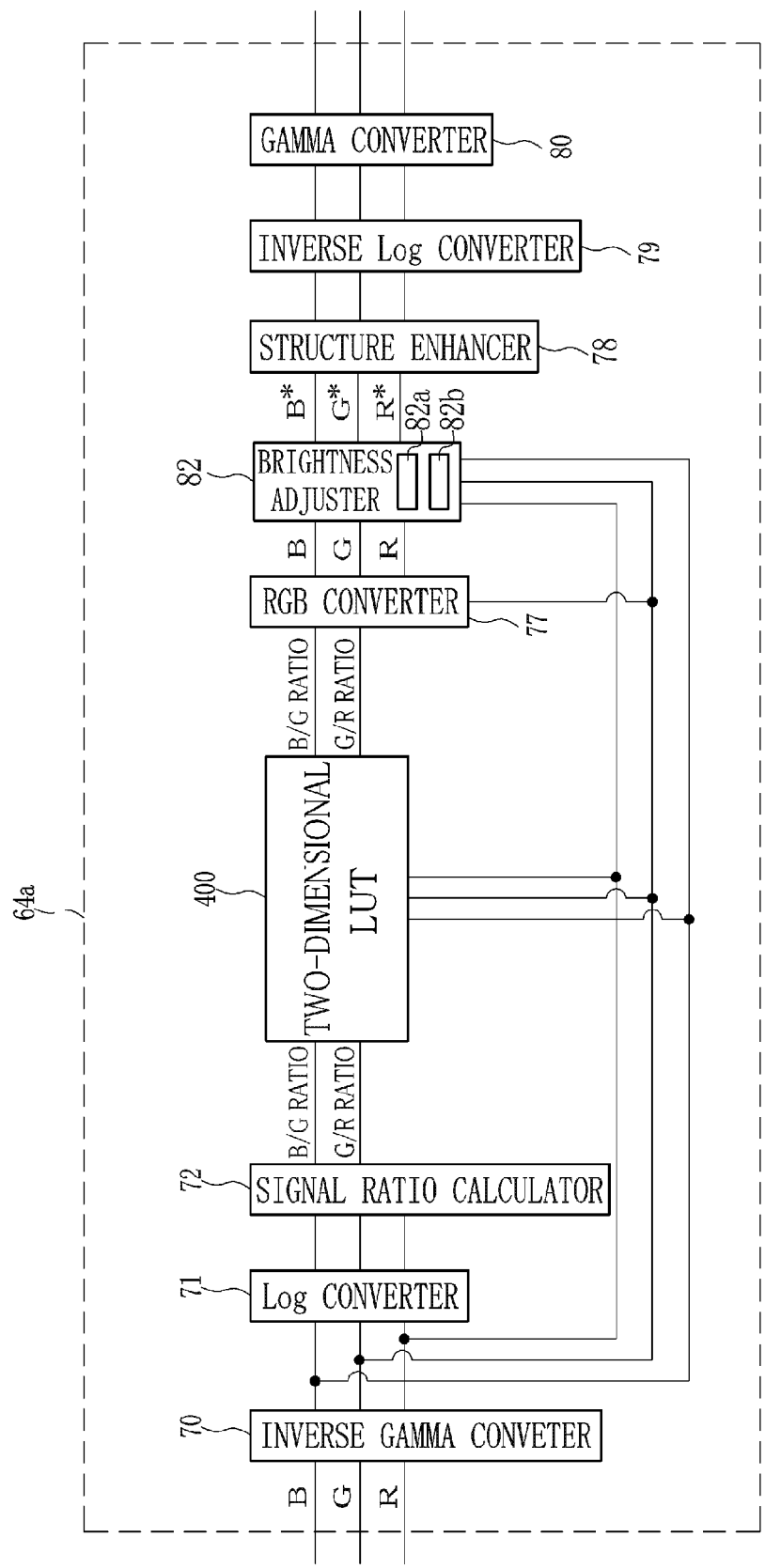
FIG. 47 is a block diagram illustrating functions of the first special image processor in which a two-dimensional LUT is used.

Note that, in the above embodiments, the four colors of light with the emission spectrums illustrated in FIG. 3 are used by way of example. The emission spectrums are not limited to this example. For example, as illustrated in FIG. 46, the green light G and the red light R may have the same spectrums as those illustrated in FIG. 3. The violet light Vs may have the center wavelength 410 to 420 nm in a wavelength range slightly shifted to a longer wavelength side than that of the violet light V in FIG. 3. The blue light Bs may have the center wavelength 445 to 460 nm in a wavelength range slightly shifted to a shorter wavelength side than that of the blue light B in FIG. 3. Note that, in the above embodiments, the first process is performed based on the B/G and G/R ratios by the first special image processor 64a. After the first process, the B/G ratio and the G/R ratio are converted into the radial coordinate r and the angular coordinate θ through the polar coordinate conversion. Then, the second process is performed based on the radial coordinate r and the angular coordinate θ converted. Thereafter, the radial coordinate r and the angular coordinate θ are converted back into the B/G ratio and the G/R ratio. Alternatively, as illustrated in FIG. 47, a two-dimensional LUT 400 may be used to directly convert the B/G and G/R ratios, without the polar coordinate conversion, into the processed B/G and G/R ratios which have been subjected to the first and second processes or the third and fourth processes.

Note that the two-dimensional LUT 400 stores the B/G and G/R ratios in association with the processed B/G and G/R ratios, which have been subjected to the first and second processes (or third and fourth processes) performed based on the B/G and G/R ratios. Note that the second special image processor 64b may use a two-dimensional LUT to perform the processing in a like manner. The first RGB image signals outputted from the inverse gamma converter 70 are inputted to the two-dimensional LUT 400. Alternatively, the first RGB image signals may be inputted to the RGB converter 77, in a manner similar to the above embodiments.

Note that, in the above embodiments, the angle θ is changed in the second process to move the first observation area and the third observation area away from each other. The first and third observation areas may be moved away from each other in a different way. For example, the radial coordinate r may be changed to move the first observation area and the third observation area away from each other. Both the radial coordinate r and the angle θ may be changed to move the first to third observation areas away from each other. In the fourth process, the coordinates which correspond to the first observation area may be changed while the coordinates which correspond to the third observation area maintained unchanged.

Note that, in the above embodiments, the B/G ratio and the G/R ratio are obtained from the first RGB image signals. The signal ratio space is formed by the B/G ratio and the G/R ratio. In the case where the first B image signal is a narrowband signal obtained from narrowband light (for example, the light with the half width of 20 nm or less) with a narrow wavelength range, the difference (distance) between the first and second observation areas and the difference (distance) between the first and third observation areas in the signal ratio space increase as compared with those of the case where the first B image signal is a broadband signal obtained from broadband light (for example, the light with the half width of more than 20 nm) with a broad wavelength range. Here, the examples of the "narrowband light" includes the "violet light V" and the "blue light B" of the first embodiment, the "blue laser beams" and the "blue-violet laser beams" of the second embodiment, "the blue narrowband light" of the third embodiment, and the "light from the blue light source" of the fourth embodiment.

Figure 48:
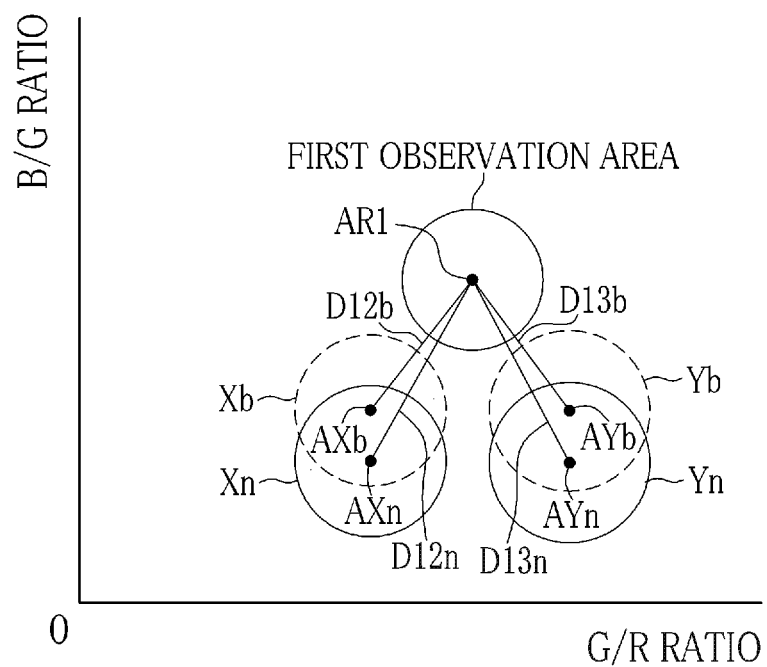
FIG. 48 is an explanatory view illustrating positions of the second and third observation areas in the feature space in the case where the first B image signal is a narrowband signal and positions of the second and third observation areas in the feature space in the case where the first B image signal is a broadband signal.

In FIG. 48, "Xn" denotes the second observation area in the case where the first B image signal is the narrowband signal. "Xb" denotes the second observation area in the case where the first B image signal is the broadband signal. "Xn" is located lower than the "Xb" in the signal ratio space. "Yn" denotes the third observation area in the case where first B image signal is the narrowband signal. "Yb" denotes the third observation area in the case where the first B image signal is the broadband signal. "Yn" is located lower than the "Yb" in the signal ratio space.

As illustrated in FIG. 48, the difference D12n between the average value AXn of "Xn" and the average value AR1 of the first observation area is greater than the difference D12b between the average value AXb of "Xb" and the average value AR1 of the first observation area. The difference D13n between the average value AYn of "Yn" and the average value AR1 of the first observation area is greater than the difference D13b between the average AYb of "Yb" and the average value AR1 of the first observation area. As described above, in the case where the first B image signal is the narrowband signal, the differences between the first observation area and the second and third observation areas are significant even before the process for expanding and compressing the radial coordinate. The difference in color between the normal portion and the atrophic portion is displayed more clearly by performing the process for expansion and compression on the first to third observation areas which are already distant from each other.

Note that, in the case where the first G image signal is the narrowband signal, the difference between the first observation area and the second observation area and the difference between the first observation area and the third observation area are greater than those of the case where the first G image signal is the broadband signal in a manner similar to the above. The narrowband signal is not limited to the first B image signal or the first G image signal described above. By using the narrowband signal for at least one of the first RGB image signals, the difference between the first and second observation areas and the difference between the first and third observation areas are greater than those of the case where all of the first RGB image signals are broadband signals. The examples of the "narrowband signal" includes the above-described signal obtained from the narrowband light and a signal obtained by a spectral estimation process described in Japanese Patent Laid-Open Publication No. 2003-93336.

Note that the present invention is applicable to various types of medical image processing device in addition to the processor devices incorporated in the endoscope systems described in the first to third embodiments and the capsule endoscope system described in the fourth embodiment.

Various changes and modifications are possible in the present invention and may be understood to be within the present invention.

What is claimed is:

1. A medical image processing device comprising:
a processing circuitry configured to:
perform an input process of a first color image signal obtained by capturing a reflection image of an object illuminated by illumination light of two or more colors;
obtain two or more pieces of color information from the first color image signal, the two or more pieces of color information being included in one of first, second, and third areas in a feature space formed by the two or more pieces of color information, according to a condition of the object;
perform a first movement process for moving coordinates within the feature space from the first, second, and third observation areas so as to move the coordinates from a specific observation area to a reference area defined in the feature space and for moving the coordinates from the two observation areas, other than the specific observation area, out of the first to third observation areas, to be away from each other, the specific observation area being one of the first to third observation areas; and
generate a medical image based on the two or more pieces of color information after subjected to the first movement process.

2. The medical image processing device according to claim 1, wherein the feature space is a Cb-Cr space formed by color difference signals Cr and Cb, being the two or more pieces of color information, or an ab space formed by color components a* and b*, being the two or more pieces of color information, of CIE Lab space.

3. The medical image processing device according to claim 2, wherein, within the feature space, the processing circuitry moves the coordinates in a parallel manner from the first, second, and third observation areas so as to move the coordinates from the specific observation area to the reference area and changes angles of the coordinates located in the two observation areas, other than the specific observation area, out of the first to third observation areas so as to move the coordinates from the two observation areas to be away from each other.

4. The medical image processing device according to claim 2, wherein the reference area includes an origin point of the feature space but excludes the two observation areas other than the specific observation area.

5. The medical image processing device according to claim 1, wherein the two or more pieces of color information are hue H and saturation S, and the feature space is an HS space formed by the hue H and the saturation S.

6. The medical image processing device according to claim 5, wherein, within the HS space, the processing circuitry moves the coordinates in a parallel manner in a saturation direction from the first, second, and third observation areas so as to move the coordinates from the specific observation area to the reference area and moves the coordinates in a hue direction from the two observation areas, other than the specific observation area, out of the first to third observation areas, to be away from each other.

7. The medical image processing device according to claim 5, wherein the reference area includes an origin point of the HS space but excludes the two observation areas other than the specific observation area.

8. The medical image processing device according to claim 1, wherein the processing circuitry further performs a second movement process a second movement process for moving the coordinates within the feature space from the second observation area to the reference area while the coordinates in the first and third observation areas are maintained unchanged and for moving the coordinates within the feature space from the third observation area while the coordinates in the first observation area are maintained unchanged.

9. The medical image processing device according to claim 8, wherein the feature space is Cb-Cr space formed by color difference signals Cr and Cb, being the two or more pieces of color information, or an ab space formed by color components a* and b*, being the two or more pieces of color information, of CIE Lab space.

10. The medical image processing device according to claim 9, wherein, in the feature space, the processing circuitry changes a radial coordinate of the coordinates in the second observation area to move the coordinates from the second observation area to the reference area while the coordinates in the first and third observation areas are maintained unchanged, and changes an angle of the coordinates in the third observation area to move the coordinates from the third observation area while the coordinates in the first observation area are maintained unchanged and while the coordinates moved from the second observation area are maintained in the reference area.

11. The medical image processing device according to claim 9, wherein the reference area includes an origin point of the feature space but excludes the first observation area and the third observation area.

12. The medical image processing device according to claim 8, wherein the two or more pieces of color information are hue H and saturation S, and the feature space is an HS space formed by the hue H and the saturation S.

13. The medical image processing device according to claim 12, wherein, within the HS space, the processing circuitry moves the coordinates in a saturation direction from the second observation area to the reference area while the coordinates in the first and third observation areas are maintained unchanged and moves the coordinates in a hue direction from the third observation area while the coordinates in the first observation area are maintained unchanged and while the coordinates moved from the second observation area are maintained in the reference area.

14. The medical image processing device according to claim 12, wherein the reference area includes an origin point of the HS space but excludes the first observation area and the third observation area.

15. The medical image processing device according to claim 8, wherein the processing circuitry is further configured to:
convert the two or more pieces of color information, which have been subjected to the first movement process or the second movement process, into a second color image signal; and
adjust a pixel value of the second color image signal based on first brightness information obtained from the first color image signal and second brightness information obtained from the second color image signal.

16. The medical image processing device according to claim 1, wherein the first color image signal is three color image signals, and, within the feature space, a difference between the first observation area and the second observation area of a case where at least one of the three color image signals is a narrowband signal is greater than a difference between the first observation area and the second observation area of a case where all of the three color image signals are broadband signals, or a difference between the first observation area and the third observation area of the case where at least one of the three color image signals is a narrowband signal is greater than a difference between the first observation area and the third observation area of the case where all of the three color image signals are broadband signals.

17. An endoscope system comprising:
a medical image processing device according to claim 8; and
a monitor which displays a first special image obtained from two or more pieces of color information processed by the first movement processor and a second special image obtained from two or more pieces of color information processed by the second movement processor.

18. A method for operating a medical image processing device comprising the steps of:
performing an input process of a first color image signal obtained by capturing a reflection image of an object illuminated by illumination light of two or more colors;
obtaining two or more pieces of color information from the first color image signal, the two or more pieces of color information being included in one of first, second, and third areas in a feature space formed by the two or more pieces of color information, according to a condition of the object;
performing a first movement process for moving coordinates within a feature space from first, second, and third observation areas so as to move the coordinates from a specific observation area to a reference area defined in the feature space and for moving the coordinates from the two observation areas, other than the specific observation area, out of the first to third observation areas, to be away from each other, the specific observation area being one of the first to third observation area; and
generating a medical image based on the two or more pieces of color information after subjected to the first movement process.

* * * * *